US012624330B2

(12) United States Patent
Nakai et al.

(10) Patent No.: US 12,624,330 B2
(45) Date of Patent: May 12, 2026

(54) CELL CULTURE METHOD, PRODUCT PRODUCING METHOD, AND CELL CULTURE DEVICE

(71) Applicant: FUJIFILM Corporation, Tokyo (JP)

(72) Inventors: Shinichi Nakai, Kanagawa (JP);
Kosuke Taniguchi, Kanagawa (JP);
Nobuyuki Haraguchi, Kanagawa (JP);
Tsukasa Ishihara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1252 days.

(21) Appl. No.: 17/104,094

(22) Filed: Nov. 25, 2020

(65) Prior Publication Data

US 2021/0147781 A1      May 20, 2021

Related U.S. Application Data

(63) Continuation of application No. PCT/JP2019/020717, filed on May 24, 2019.

(30) Foreign Application Priority Data

Jun. 27, 2018      (JP) ................................. 2018-122322

(51) Int. Cl.
*C12N 5/00* (2006.01)
*C07K 16/00* (2006.01)
*C12M 1/00* (2006.01)
*C12M 3/02* (2006.01)

(52) U.S. Cl.
CPC ............. *C12M 29/06* (2013.01); *C07K 16/00* (2013.01); *C12M 29/10* (2013.01); *C12N 5/00* (2013.01); *C07K 2317/14* (2013.01); *C12M 3/02* (2013.01); *C12M 29/08* (2013.01); *C12N 2500/00* (2013.01); *C12N 2500/02* (2013.01); *C12N 2511/00* (2013.01)

(58) Field of Classification Search
CPC ... C12N 5/00; C12N 2500/02; C12N 2511/00
See application file for complete search history.

(56) References Cited

U.S. PATENT DOCUMENTS

| | | | |
|---|---|---|---|
| 2009/0188211 A1 | 7/2009 | Galliher et al. | |
| 2009/0280565 A1 | 11/2009 | Jolicoeur et al. | |
| 2010/0112700 A1* | 5/2010 | Shaaltiel | C12M 23/28 |
| | | | 435/410 |
| 2011/0312087 A1* | 12/2011 | Khan | C12M 21/08 |
| | | | 435/325 |
| 2012/0244602 A1 | 9/2012 | Okumura et al. | |
| 2013/0330768 A1* | 12/2013 | Stahn | C07K 16/00 |
| | | | 435/372 |
| 2016/0032232 A1 | 2/2016 | Khan | |
| 2016/0244710 A1 | 8/2016 | Wood et al. | |
| 2018/0327705 A1 | 11/2018 | Matsuka et al. | |

FOREIGN PATENT DOCUMENTS

| | | | |
|---|---|---|---|
| CN | 102725392 A | 10/2012 |
| EP | 2 216 395 A1 | 8/2010 |
| JP | 5-503848 A | 6/1993 |
| JP | 5-292942 A | 11/1993 |
| JP | 2000-106864 A | 4/2000 |
| JP | 2012-517217 A | 8/2012 |
| JP | 2016-536122 A | 11/2016 |
| WO | WO 91/11508 A1 | 8/1991 |
| WO | WO 2011/070791 A1 | 6/2011 |
| WO | WO 2017/115855 A1 | 7/2017 |
| WO | WO 2018/025686 A1 | 2/2018 |

OTHER PUBLICATIONS

Porex, Technical Data sheets for Porex Hydrophobic Small Pore Size Sheet 9619, Porex Hydrophobic Medium Pore Size Sheet 4920, and Porex Hydrophobic Large Pore Size Sheet 4903, https://www.porex.com, accessed Aug. 1, 2024 and webpage copyright 2024 (Year: 2024).*
Extended European Search Report for corresponding European Application No. 19824606.8, dated May 21, 2021.
Hesse et al., "Comparison of a Production Process in a Membrane-Aerated Štirred Tank and up to 1000-L Airlift Bioreactors Using BHK-21 Cells and Chemically Defined Protein-Free Medium," Biotechnology Progress, vol. 19, 2003, pp. 833-843, 11 pages total.
International Preliminary Report on Patentability and Written Opinion of the International Searching Authority with an English translation (forms PCT/IB/373 and PCT/ISA/237), dated Dec. 29, 2020, for corresponding International Application No. PCT/JP2019/020717.
International Search Report (form PCT/ISA/210), dated Aug. 27, 2019, for corresponding International Application No. PCT/JP2019/020717, with an English translation.
Chinese Office Action and Search Report for corresponding Chinese Application No. 201980041529.9, dated Jul. 26, 2023, with English translation.

(Continued)

*Primary Examiner* — Emily A Cordas

(74) *Attorney, Agent, or Firm* — Birch, Stewart, Kolasch & Birch, LLP

(57) ABSTRACT

Provide are a cell culture method which includes using a culture vessel which contains a cell suspension containing cells and discharging a gas including 30% by volume or more of oxygen into the cell suspension from a sparger disposed in the culture vessel to culture the cells, in which an average hole diameter in a gas discharge portion in the sparger is 1 μm or more and 300 μm or less, and a surface area A (m²) in the gas discharge portion in the sparger, a volume X (m³) of the cell suspension in the culture vessel, and a flow rate Q (m³/min) of the gas that is discharged from the sparger satisfy a specific relationship, a product producing method including the cell culture method, and a cell culture device that enables the cell culture method.

17 Claims, 3 Drawing Sheets

(56)     References Cited

OTHER PUBLICATIONS

Huang et al., "Aeration Techniques of Animal/Plant Cell or Tissue Suspension Cultures in Bioreactor," Progress in Modern Biomedicine, vol. 7, No. 2, 2007, pp. 273-279, with English abstract.
Xie et al., "Optimization of Condition for Culture of CHO Cells by Tubespin, a Disposable High-throughput Bioreactor," Chin J Biologicals, vol. 24, No. 6, Jun. 2011, pp. 715-719, with English abstract.
Japanese Office Action for Japanese Application No. 2020-527292, dated Sep. 7, 2021, with English translation.

* cited by examiner

CELL CULTURE METHOD, PRODUCT PRODUCING METHOD, AND CELL CULTURE DEVICE

CROSS-REFERENCE TO RELATED APPLICATION

This application is a continuation application of International Application No. PCT/JP2019/020717, filed May 24, 2019, the disclosure of which is incorporated herein by reference in its entirety. Further, this application claims priority from Japanese Patent Application No. 2018-122322, filed Jun. 27, 2018, the disclosure of which is incorporated herein by reference in their entirety.

BACKGROUND OF THE INVENTION

1. Field of the Invention

The present disclosure relates to a cell culture method, a product producing method, and a cell culture device.

2. Description of the Related Art

Cell culture is performed for the purpose of increasing the number of cells having useful properties, causing cells to produce a product or the like.

As the conventional cell culture method or device used for cell culture, JP1993-503848A (JP-H05-503848A), WO2011/070791A, and JP2016-536122A are mentioned.

JP1993-503848A (JP-H05-503848A) discloses a method for supplying gaseous nutrients on a bubble form to cells in a bioreactor at least partially filled with a medium, which is characterized by the point that the retention time of the bubble is equal to the dissolution time of the gaseous nutrients in the medium.

WO2011/070791A discloses a culture method for culturing cells or microorganisms by dissolving oxygen or carbon dioxide in a culture solution containing nutrients, including a process of culturing cells or microorganisms by supplying a gas including oxygen or carbon dioxide to a porous body to generate bubbles having a 50% diameter of 200 μm or less in a culture solution, the 50% diameter being obtained in the volume-based size distribution and the culture solution containing at least one of a protein hydrolyzate or a cyto-protective agent for protecting cells, thereby dissolving oxygen or carbon dioxide in the culture solution containing nutrients.

JP2016-536122A discloses an aeration device as an aeration device used at the time of cell culture, which includes a base member and a plurality of aeration elements that are installed attachably and detachably to the base member, each of the aeration elements including a gas permeable material and an inlet which is configured to connect to a gas source and being in fluid communication with the gas permeable material.

SUMMARY OF THE INVENTION

Cell culture may be performed while discharging a gas including oxygen into a cell suspension containing cells. It is speculated that the discharge causes oxygen to be supplied to the cell suspension.

In a case of performing cell culture, there is a demand to increase the cell concentration in the cell suspension as high as possible. Particularly, in the production of biomedical drugs such as in a case where a product (for example, antibody) is produced by cell culture, it is important to increase the cell concentration in the cell suspension in order to improve the productivity of the product.

For this reason, it is necessary to dissolve a large amount of oxygen in the cell suspension and supply a sufficient amount of oxygen to cells having a high cell concentration.

As a method of discharging oxygen to a cell suspension, a method in which a sparger is installed in the culture vessel is known.

In order to discharge a sufficient amount of oxygen to cells, a technique of dissolving a large amount of oxygen in a cell suspension was used as a general technique. In this method, an average hole diameter in a gas discharge portion in a sparger is minimized to improve the solubility of oxygen and the flow rate of the gas including oxygen is increased (refer to, for example, JGC Technical Journal, Vol. 01, No. 01 (2011), Application of microbubbles to culture).

However, the inventors of the present invention noticed that in a case where the cell suspension volume is large (for example, the cell suspension volume is 0.5 m³ or more) as in the case such as a mass production scale, it is difficult to culture cells at a high cell concentration with the method such as the method described above, since a sufficient amount of oxygen for cell culture cannot be dissolved in the cell suspension and the damage to cells is large.

This is presumably because oxygen is difficult to be dissolved in the cell suspension by the above method, the oxygen transfer capacity coefficient kLa (hereinafter, may be referred to as "kLa") is not so high, the damage to cells due to the discharged bubbles is increased as the average hole diameter of the gas discharge portion in the sparger is decreased, and the damage to cells is increased due to the discharge of a gas including a large amount of oxygen.

Specifically, it is speculated as follows; when a gas including oxygen is discharged from the sparger, cells are damaged by the energy transferred when bubbles collide with the cells or the bubbles break themselves, but the energy increases as the sparger hole diameter is decreased, that is, as the bubbles having small diameters are present, and as the flow rate of the gas including oxygen is increased, whereby the damage to cells is increased.

Here, the above-described kLa is a proportional coefficient of a rate equation which represents a dissolution rate of oxygen gas in the cell suspension. The higher the kLa is, the more rapidly oxygen is dissolved in the cell suspension, whereby more oxygen can be supplied to the cell suspension, and thus cells can be cultured at a high cell concentration. It is speculated that kLa increases as the bubble diameter decreases.

That is, increasing kLa and suppressing the damage to cells have a trade-off relationship in the related art, and these were hardly achieved compatibly.

An object of the present invention is to provide a cell culture method in which cell culture is possible at a high cell concentration even in a case where a cell suspension volume is large, and the damage to cells is suppressed, a product producing method including the cell culture method, and a cell culture device that enables the cell culture method.

Means for solving the above problems include the following aspects.

<1> A cell culture method comprising: using a culture vessel which contains a cell suspension containing cells; and discharging a gas including 30% by volume or more of oxygen into the cell suspension from a sparger disposed in the culture vessel to culture the cells, in which an average hole diameter in a gas discharge portion in the sparger is 1 μm or more and 300 μm or less, and a surface area A (m$^2$) of the gas discharge portion in the sparger, a volume X (m$^3$) of the cell suspension in the culture vessel, and a flow rate Q (m$^3$/min) of the gas that is discharged from the sparger satisfy Expression 1-1, Expression 1-2, and Expression 1-3.

$$0.004 \leq A/X \leq 0.1 \qquad \text{Expression 1-1}$$

$$X \geq 0.5 \qquad \text{Expression 1-2}$$

$$0.001 \leq Q/X \leq 0.1 \qquad \text{Expression 1-3}$$

<2> The cell culture method according to <1>, in which in a case where the cell suspension in the culture vessel is replaced with a measurement solution which is pure water containing 1 g/L of poloxamer 188, 7 g/L of sodium chloride, and 2 g/L of sodium hydrogen carbonate, an air gas having the same flow rate as the Q (m$^3$/min) in the culture is sent from the sparger to the measurement solution, and a bubble diameter distribution in a gas discharge outlet of the sparger is measured, a volume average bubble diameter Dv (μm) of bubbles of the air gas satisfies Expression 2-1.

$$50 \leq Dv \leq 800. \qquad \text{Expression 2-1}$$

<3> The cell culture method according to <1> or <2>, in which in a case where the cell suspension in the culture vessel is replaced with a measurement solution which is pure water containing 1 g/L of poloxamer 188, 7 g/L of sodium chloride, and 2 g/L of sodium hydrogen carbonate, an air gas having the same flow rate as the Q (m$^3$/min) in the culture is sent from the sparger to the measurement solution, and a bubble diameter distribution in a gas discharge outlet of the sparger is measured, in the bubble diameter distribution, a proportion of a cumulative volume of air bubbles having a bubble diameter of 20 μm or more and 500 μm or less is 30% by volume or more of a total volume of the bubbles in the bubble diameter distribution.

<4> The cell culture method according to any one of <1> to <3>, in which an oxygen transfer capacity coefficient kLa (hr$^{-1}$) by the sparger in the culture is 15 or more.

<5> The cell culture method according to any one of <1> to <4>, in which in a case where the cell suspension in the culture vessel is replaced with a measurement solution which is pure water containing 1 g/L of poloxamer 188, 7 g/L of sodium chloride, and 2 g/L of sodium hydrogen carbonate, an air gas having the same flow rate as the Q (m$^3$/min) in the culture is sent from the sparger to the measurement solution, and a bubble diameter distribution in a gas discharge outlet of the sparger is measured, the Q (m$^3$/min), the A (m$^2$), a density ρL (kg/m$^3$) of the measurement solution, a density ρg (kg/m$^3$) of the air gas, a viscosity μL (kg/m/s) of the measurement solution, and a gravitational acceleration g (m/s$^2$) satisfy Expression 3-1.

$$0.1 < (Q/A/60)/[\{3 \times 10^{-8} \times (\rho L - \mu g) \times g\}/(18 \times \mu L)\}]5 \qquad \text{Expression 3-1}$$

<6> The cell culture method according to any one of <1> to <5>, in which in the culture, the Q (m$^3$/min) and the A (m$^2$) satisfy Expression 4-1.

$$0.1 \leq Q/A \leq 5 \qquad \text{Expression 4-1}$$

<7> The cell culture method according to any one of <1> to <6>, in which in a case where the cell suspension in the culture vessel is replaced with a measurement solution which is pure water containing 1 g/L of poloxamer 188, 7 g/L of sodium chloride, and 2 g/L of sodium hydrogen carbonate, an air gas having the same flow rate as the Q (m$^3$/min) in the culture is sent from the sparger to the measurement solution, and a bubble diameter distribution in a gas discharge outlet is measured, a liquid level ZL (m) from an inner bottom surface of the culture vessel to an upper surface of the cell suspension in the culture, a height Zs (m) from the inner bottom surface of the culture vessel to a sparger installation surface, a volume average bubble diameter Dv (μm) of bubbles in the bubble diameter distribution, a density ρL (kg/m$^3$) of the measurement solution, a density ρg (kg/m$^3$) of the air gas, a gravitational acceleration g (m/s$^2$), and a viscosity μL (kg/m/s) of the measurement solution satisfy Expression 5-1.

$$2 < (ZL - Zs)/\{Dv^2 \times 10^{-12} \times (\rho L - \rho g) \times g/(18 \times \mu L)\} < 300 \qquad \text{Expression 5-1}$$

<8> The cell culture method according to any one of <1> to <7>, in which the X (m$^3$), a liquid level ZL (m) from an inner bottom surface of the culture vessel to an upper surface of the cell suspension, and a height Zs (m) from the inner bottom surface of the culture vessel to a sparger installation surface satisfy Expression 6-1 and Expression 6-2.

$$Zs/ZL \leq 0.5 \qquad \text{Expression 6-1}$$

$$0.5 < ZL/(4 \times X/ZL/3.14)^{0.5} \leq 4 \qquad \text{Expression 6-2}$$

<9> The cell culture method according to any one of <1> to <8>, in which a cell concentration in the cell suspension is $4 \times 10^7$ cells/mL or more.

<10> The cell culture method according to any one of <1> to <9>, in which a method for culturing cells is the perfusion culture.

<11> The cell culture method according to any one of <1> to <10>, in which the culture vessel is a single-use culture tank.

<12> The cell culture method according to any one of <1> to <11>, in which the sparger is a sintered metal sparger.

<13> The cell culture method according to any one of <1> to <12>, in which a shape of the gas discharge portion of the sparger is a circular plane shape, a polygonal plane shape, or a cylinder shape.

<14> The cell culture method according to any one of <1> to <13>, in which a plurality of the spargers are included as the sparger.

<15> The cell culture method according to any one of <1> to <13>, in which the sparger is configured to include a plurality of units each including one or more spargers, and the flow rate of the gas is adjusted for each of the units.

<16> A product producing method comprising: culturing cells with the cell culture method according to any one of <1> to <15>, and obtaining a product produced by the cultured cells.

<17> The product producing method according to <16>, in which the product is an antibody.

<18> A cell culture device comprising: a culture vessel which contains a cell suspension containing cells, in which the cells are cultured, and a sparger for discharging a gas including 30% by volume or more of oxygen into the cell suspension in the culture vessel, in which an average hole diameter of the sparger is 1 μm or more and 300 μm or less, and an area A (m$^2$) of the sparger and a volume Xmax (m$^3$) of the cell suspension with which the culture vessel can be maximally filled satisfy Expression 7-1 and Expression 7-2.

$$0.004 \leq A/Xmax \leq 0.1 \qquad \text{Expression 7-1}$$

$$Xmax \geq 0.5 \qquad \text{Expression 7-2}$$

<19> The cell culture device according to <18>, in which a liquid level ZLmax (m) from an inner bottom surface of the culture vessel to an upper surface of the cell suspension in a case where the culture vessel is maximally filled with the cell suspension, and a height Zs (m) from the inner bottom surface of the culture vessel to a sparger installation surface satisfy Expression 8-1.

$$2 \leq (ZLmax - Zs)/0.02 \leq 300 \qquad \text{Expression 8-1}$$

<20> The cell culture device according to <18> or <19>, in which the Xmax $(m^3)$, a liquid level ZLmax (m) from an inner bottom surface of the culture vessel to an upper surface of the cell suspension in a case where the culture vessel is maximally filled with the cell suspension, and a height Zs (m) from the inner bottom surface of the culture vessel to a sparger installation surface satisfy Expression 9-1 and Expression 9-2.

$$Zs/ZLmax \leq 0.5 \qquad \text{Expression 9-1}$$

$$0.5 < ZLmax/\{(4 \times Xmax/ZLmax/3.14)^{0.5}\} \leq 4 \qquad \text{Expression 9-2}$$

<21> The cell culture device according to any one of <18> to <20>, in which the culture vessel is a single-use culture tank.

<22> The cell culture device according to any one of <18> to <21>, in which the sparger is a sintered metal sparger.

<23> The cell culture device according to any one of <18> to <22>, in which a shape of the gas discharge portion of the sparger is a circular plane shape, a polygonal plane shape, or a cylinder shape.

<24> The cell culture device according to any one of <18> to <23>, in which a plurality of the spargers are included as the sparger.

<25> The cell culture device according to any one of <18> to <23>, in which the sparger is configured to include a plurality of units each including one or more spargers, and a flow rate of the gas is adjustable for each of the units.

<26> The cell culture device according to any one of <18> to <25>, in which the cell culture device is a perfusion cell culture device.

According to the embodiment of the present invention, a cell culture method in which cell culture is possible at a high cell concentration even in a case where a cell suspension has a large volume, and the damage to cells is suppressed, a product producing method including the cell culture method, and a cell culture device that enables the cell culture method are provided.

DESCRIPTION OF THE PREFERRED EMBODIMENTS

Figure 1C:
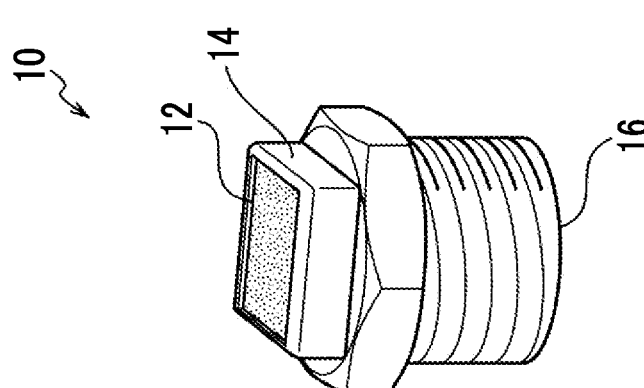
FIGS. 1A-C are schematic diagrams of formation examples of sintered metal spargers that are examples of spargers used in the present disclosure.

Hereinafter, a cell culture method, a product producing method, and a cell culture device according to the present disclosure will be described. However, the embodiments according to the present disclosure are not limited to the following embodiments and can be implemented with appropriate modifications.

In the present disclosure, the numerical range represented by using "to" means a range including the numerical values before and after "to" as the minimum value and the maximum value, respectively.

In the numerical ranges described stepwise in the present disclosure, the upper limit value or the lower limit value described in a numerical range may be replaced with the upper limit value or the lower limit value of the numerical range described stepwise in other stages. Further, in the numerical ranges described in the present disclosure, the upper limit value or the lower limit value of a numerical range may be replaced with the value shown in Examples.

In the present disclosure, a combination of two or more preferred aspects is a more preferred aspect.

In the present disclosure, in a case where there are a plurality of substances corresponding to each component, unless otherwise particularly specified, the amount of each component means the total amount of the plurality of substances.

In the present disclosure, the identical reference numeral is given to the same constituent elements, and description thereof may be omitted.

In the present disclosure, the drawings illustrate one example of preferred aspects, and the invention according to the present disclosure is not limited by the contents of the drawings.

In the present disclosure, the term "process" includes not only an independent process but also a process that cannot be clearly distinguished from other processes, as long as the intended purpose of the process is achieved.

(Cell Culture Method)

The cell culture method according to the present disclosure includes using a culture vessel which contains a cell suspension containing cells and discharging a gas including 30% by volume or more of oxygen into the cell suspension from a sparger disposed in the culture vessel to culture the cells (hereinafter, also referred to as "cell culture process")), in which an average hole diameter in a gas discharge portion in the sparger is 1 μm or more and 300 μm or less, and a surface area A $(m^2)$ in the gas discharge portion in the sparger, a volume X $(m^3)$ of the cell suspension in the culture vessel, and a flow rate Q $(m^3/min)$ of the gas that is discharged from the sparger satisfy Expression 1-1, Expression 1-2, and Expression 1-3.

$$0.004 \leq A/X \leq 0.1 \qquad \text{Expression 1-1}$$

$$X \geq 0.5 \qquad \text{Expression 1-2}$$

$$0.001 \leq Q/X \leq 0.1 \qquad \text{Expression 1-3}$$

The cell culture method according to the present disclosure includes using a culture vessel which contains a cell suspension containing cells; and discharging a gas including 30% by volume or more of oxygen into the cell suspension from a sparger disposed in the culture vessel to culture the cells.

It is speculated that in a case of discharging the gas including 30% by volume or more of oxygen, oxygen is discharged into the cell suspension, which enables cell culture at a high cell concentration.

Further, the average hole diameter of the gas discharge portion used in the cell culture method according to the present disclosure is 1 μm or more and 300 μm or less. It is speculated that in a case where the average hole diameter is 1 μm or more, the bubble diameter of the bubbles of the gas including oxygen is not too small, but the damage to cells is suppressed.

Further, it is speculated that in a case where the average hole diameter is 300 μm or less, the bubble diameter is not too large, but kLa easily increases, and thus cell culture can be performed at a high cell concentration.

Furthermore, in the cell culture method according to the present disclosure, the A (m$^2$) and the X (m$^3$) satisfy Expression 1-1 and Expression 1-2.

Here, in a case where the capacity of the conventional culture vessel is changed, for example, in a case where the length of each side of the culture vessel is increased by 10 times, the cell suspension volume is increased by 10×10×10=1,000 times. In that case, it is common to make the length of each side of the sparger 10 times, thereby obtaining the area of the sparger, increased by 10×10=100 times (scaling law).

On the other hand, in the cell culture method in the present disclosure, the A/X has a value within a specific range. This means that, for example, In a case where the cell suspension volume X is increased by 1,000 times, the surface area A of the gas discharge portion in the sparger is also increased by 1,000 times.

Further, in a case where the Q/X is 0.001 or more, it is speculated that oxygen necessary for cell culture is sufficiently supplied to the cell suspension and the cell concentration increases easily.

Further, in a case where the Q/X is 0.1 or less, it is speculated that the damage to cells is easily suppressed.

That is, the cell culture method according to the present disclosure is based on the new findings that in a case where a liquid volume X of the cell suspension in the culture vessel, a surface area A of the gas discharge portion in the sparger, a flow rate Q of the gas, and an average hole diameter of the gas discharge portion in the sparger are adjusted depending on the cell suspension volume, cell culture can be performed at a high cell concentration while suppressing the damage to cells even in a case where the X is a large volume of 0.5 m$^3$ or more.

All of JP1993-503848A (JP-S05-503848A), WO2011/070791A, and JP2016-536122A do not describe or suggest the technical idea of the cell culture method according to the present disclosure, in which the A/X is set within a specific range and an average hole diameter of the gas discharge portion in the sparger is set within a specific range. In addition, all of them do not describe or suggest the effects of the cell culture method according to the present disclosure, with which cell culture can be performed at a high cell concentration while suppressing the damage to cells by setting the A/X and the average hole diameter to a specific value.

Hereinafter, each requirement in the cell culture method according to the present disclosure will be described.
<Cell Culture Process>

The cell culture method according to the present disclosure includes a cell culture process.

In the cell culture process, a cell culture vessel which contains a cell suspension containing cells and includes a sparger for discharging a gas including 30% by volume or more of oxygen is used.
[Culture Vessel]

As the culture vessel, a general culture device (also referred to as a bioreactor), a known vessel used in the general culture device, or another suitable vessel can be used without particular limitation. As the culture device, a fermenter type tank culture device, an air lift type culture device, a culture flask type culture device, a spinner flask type culture device, a microcarrier type culture device, a fluidized bed type culture device, a hollow fiber type culture device, a roller bottle type culture device, a filled-tank type culture device, or the like can be used.

In addition, the culture vessel is preferably a single-use culture tank from the viewpoint of homogenizing the culture environment or the like.
[Sparger]

The culture vessel includes a sparger for discharging a gas including 30% by volume or more of oxygen.

The gas including 30% by volume or more of oxygen is not particularly limited, but a gas including 50% by volume or more of oxygen is preferable, a gas including 70% by volume or more of oxygen is more preferable, and a gas including 90% by volume or more of oxygen is still more preferable, and pure oxygen gas is particularly preferable.

The culture vessel in the present disclosure may further include a sparger that discharges a gas including another gas (for example, air and CO$_2$ gas) in addition to the sparger that discharges the gas including 30% by volume or more of oxygen.

In the present disclosure, in a case of simply being described as "sparger", this means a "sparger in which the average hole diameter of the gas discharge portion is 1 μm or more and 300 μm or less and which discharges a gas including 30% by volume or more of oxygen, unless otherwise particularly specified.

That is, in the calculation of the surface area A of the gas discharge portion in the sparger, the flow rate Q (m3/min) of the gas discharged from the sparger, and the like, a sparger having an average hole diameter which is out of the above range and a sparger which discharges a gas including the other gas described above are not included.

As the sparger, any known sparger can be used without particular limitation as long as it satisfies the above-described average hole diameter and the above-described A/X. Examples of the sparger include a nozzle sparger having a nozzle shape and discharging bubbles from an opening, a ring sparger having a cylindrical ring shape with holes and discharging bubbles from the holes, a sparger using a gas permeable sheet or a non-woven polymer material, and a sintered metal sparger having a sintered metal filter at the bubble discharge portion. Among them, a sintered metal sparger is preferable from the viewpoint of easily satisfying the above-described requirement of the average hole diameter.

As the sintered metal filter in the sintered metal sparger, for example, a filter obtained by sintering fine powder of copper, nickel, titanium, tantalum, aluminum, platinum, tungsten carbide, titanium carbide, or stainless steel, or an alloy including these is used.

Figure 1B:
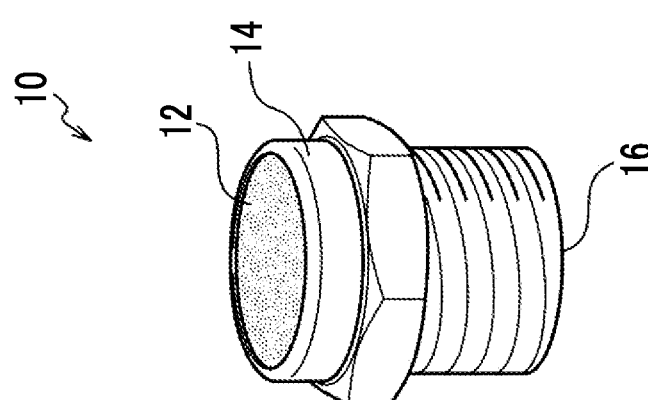
Figure 1A:
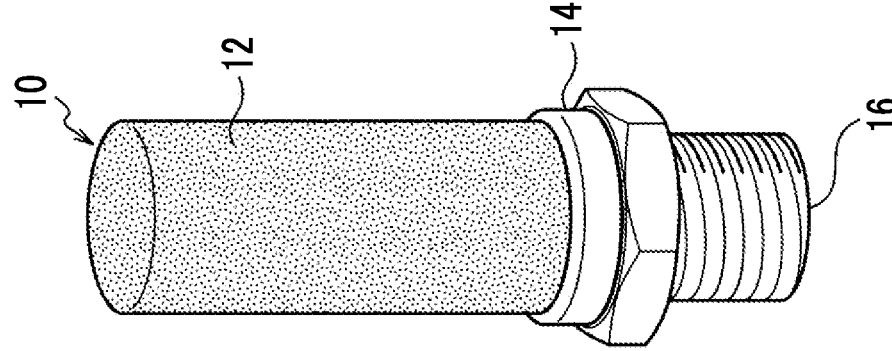

In FIGS. 1A-C, schematic diagrams of formation examples of sintered metal spargers that are examples of spargers used in the present disclosure are illustrated.

In FIG. 1A, a sintered metal sparger 10 includes a cylinder-shaped sintered metal filter 12, a support portion 14, and a gas supply portion 16. The sintered metal filter 12 is in contact with a cell suspension in the culture vessel, and the gas supplied from the gas supply portion 16 is discharged into the cell suspension through the sintered metal filter 12.

In FIG. 1B, the sintered metal sparger 10 has the same configuration as that of the sintered metal sparger 10 in FIG. 1A except that the sintered metal filter 12 has a circular plane shape.

In FIG. 1C, the sintered metal sparger 10 has the same configuration as that of the sintered metal sparger 10 in FIG. 1A except that the sintered metal filter 12 has a polygonal (quadrate) plane shape.

Here, in FIGS. 1A-C, the surface area A of the gas discharge portion in the sparger in the present disclosure refers to the surface area ($m^2$) of the portion of the sintered metal filter 12 in the sintered metal sparger 10, from which the gas is discharged. Specifically, the surface area A refers to the surface area of the cylinder-shaped sintered metal filter 12 in FIG. 1A, the area of the circle having the circular plane shape in FIG. 1B, or the area of the polygon having the polygonal plane shape in FIG. 1C.

In a nozzle sparger or a ring sparger that does not have the sintered metal filter 12, the surface area A of the gas discharge portion in the sparger refers to the area of the opening of the sparger.

The gas discharge portion in the present disclosure refers to the sintered metal filter 12 in the sintered metal sparger 10 or the opening in the nozzle sparger or the ring sparger.

The shape of the gas discharge portion in the sparger in the present disclosure is preferably a circular plane shape, a polygonal plane shape, or a cylinder shape.

Among these, a circular plane shape is preferable since bubbles can be uniformly ejected and coalescence of bubbles is suppressed.

In addition, one of the preferred aspects in the present disclosure is an aspect in which the culture vessel includes a plurality of spargers.

In a case where the culture vessel includes a plurality of spargers, the shapes of the gas discharge portions of each sparger may be the same or different. For example, regarding the shape of the gas discharge portion, a sparger having a circular plane shape and a sparger having a polygonal plane shape may be used in combination. In a case where spargers having a gas discharge portion different in shape from each other are used in combination, it is preferable to use a combination of at least two of a circular plane shape, a polygonal plane shape, and a cylinder shape.

The number of spargers in the above aspect is not particularly limited, but is preferably 2 to 100, more preferably 2 to 50, and still more preferably 2 to 20.

In addition, another of the preferred aspects in the present disclosure is an aspect in which the sparger is configured to include a plurality of units each including one or more spargers, and the flow rate of the gas is adjustable for each of the units.

In this aspect, the number of spargers included in each of the units is not particularly limited, but is preferably 1 to 50, more preferably 1 to 20, and still more preferably 2 to 10.

In addition, in this aspect, the number of units is not particularly limited, but is preferably 2 to 20, more preferably 2 to 10, and still more preferably 2 to 5.

Figure 2:
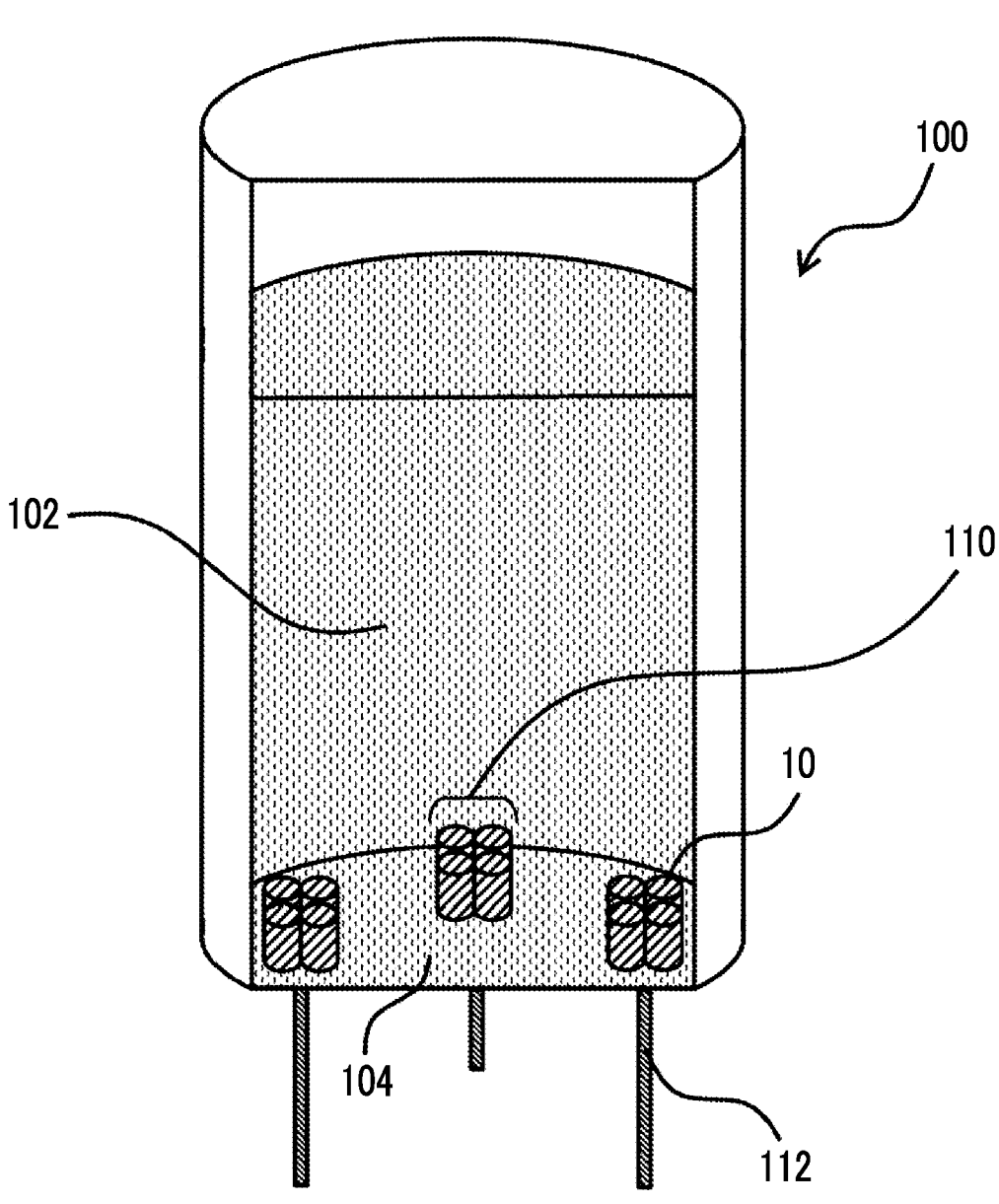
FIG. 2 is a schematic cross-sectional perspective diagram illustrating an example of an aspect in which a culture vessel includes a plurality of spargers.

FIG. 2 is a schematic cross-sectional perspective view illustrating an example of an aspect in which a culture vessel includes a plurality of spargers.

FIG. 2 is a cross-sectional view taken along a plane including the vertical direction of the culture vessel.

In FIG. 2, a culture vessel 100 contains a cell suspension 102. Further, three sparger units 110 each including four spargers 10 are formed on an inner bottom surface 104 of the culture vessel 100. The sparger 10 is the sparger illustrated in FIG. 1A, in which the gas supply portion has a cylinder shape. A gas supply portion 112 is coupled to each sparger unit 110, and the gas supplied from each gas supply portion 112 is discharged from each sparger unit 110. By adjusting the amount of gas supplied to each of the plurality of gas supply portions 112, the flow rate of the gas can be adjusted for each unit.

In a case where the culture vessel includes a plurality of spargers, the surface area A refers to the total value of the surface areas of all the spargers.

In addition, in the present disclosure, the average hole diameter of the gas discharge portion in the sparger refers to the average hole diameter of the sintered metal filter 12 in the sintered metal sparger 10.

The average hole diameter of the sintered metal filter 12 can be determined from the 95% separated particle diameter. That is, the average hole diameter of the sintered metal filter 12 can be calculated by performing a filtration test using standard particles and calculating a particle diameter with a rejection rate of 95% (that is, a 95% separated particle diameter in a particle permeation test).

In a nozzle sparger or a ring sparger that does not have the sintered metal filter 12, the surface area A of the gas discharge portion in the sparger refers to the sum of the areas of the openings of the nozzle. In this case, the average hole diameter refers to the average value of the hole diameters of the openings of the nozzle.

The hole diameter of the opening can be obtained by taking an image of the opening at an appropriate magnification and analyzing the image. In a case where the shape of the opening is not a circle, the hole diameter is calculated as an equivalent circle diameter. In the present disclosure, the equivalent circle diameter is a diameter of a circle having an area equal to the area of a plane such as an opening.

In a case where the culture vessel includes a plurality of spargers, the average hole diameter of the gas discharge portion in at least one sparger may be 1 μm or more and 300 μm or less. However, the total value of the surface area of the gas discharge portion in the sparger which satisfies the above-described requirement of the average hole diameter is preferably 60% by area or more, more preferably 80% by area or more, and still more preferably 90% by area or more, with respect to the total value of the surface area of the gas discharge portions of all spargers that discharge a gas including 30% by volume or more of oxygen contained in the culture vessel.

In addition, In a case where the culture vessel includes two or more spargers having sintered metal filters having different average hole diameters, the average hole diameter of each sintered metal filter is weighted by the surface area ratio in each sparger so that the average hole diameter of the gas discharge portions in the spargers in the entire culture vessel is calculated.

Specifically, in a case where one sparger which includes a gas discharge portion having an average hole diameter of 10 μm and a surface area of 0.01 $m^2$ and one sparger which includes a gas discharge portion having an average hole diameter of 100 μm and a surface area of 0.02 $m^2$, are included, the surface area A is 0.03 $m^2$, and the average hole diameter of the gas discharge portions of the spargers in the entire culture vessel is calculated as (10 μm×0.01 $m^2$+100 μm×0.02 $m^2$)/(0.01 $m^2$+0.02 $m^2$)=70 μm.

Average Hole Diameter of Gas Discharge Portion

The average hole diameter of the gas discharge portion in the sparger is preferably 1 μm or more, more preferably 2 μm or more, and still more preferably 10 μm or more, from the viewpoint of suppressing cell damage.

In addition, the average hole diameter is preferably 300 μm or less, more preferably 200 μm or less, and still more preferably 100 μm or less, from the viewpoint of increasing kLa to increase the concentration of cultured cells.

In a case where the culture vessel includes a plurality of spargers, the average hole diameter of the gas discharge portion of the spargers in the entire culture vessel, which is weighted by the surface area, is preferably within the above range. It is more preferable that the average hole diameter of each of the plurality of spargers is within the above range.

Further, the opening ratio of the sparger is preferably 5% or more, more preferably 10% or more, and still more preferably 15% or more, from the viewpoint of suppressing coalescence of bubbles in the gas discharge portion of the sparger, suppressing an increase in bubble diameter, and easily increasing kLa. Further, the opening ratio of the sparger is preferably 80% or less, more preferably 60% or less, and still more preferably 50% or less, from the viewpoint of suppressing the uneven ejection of bubbles from the sparger, increasing kLa, and easily suppressing the damage to cells. The opening ratio of the sparger can be calculated as follows, by measuring the density of the material used for the sparger and the density of the sparger itself.

$$\text{Opening ratio of sparger (\%)}=\text{(density of material used for sparger}-\text{density of sparger itself)/density of material used for sparger}\times 100$$

Surface Area A of Gas Discharge Portion and Volume X of Cell Suspension

The surface area A ($m^2$) of the gas discharge portion in the sparger and the volume Xm ($m^3$) of the cell suspension in the culture vessel satisfy Expression 1-1 and Expression 1-2.

$$0.004 \leq A/X \leq 0.1 \qquad \text{Expression 1-1}$$

$$X \geq 0.5 \qquad \text{Expression 1-2}$$

Here, the A/X may be 0.004 or more, is preferably 0.006 or more, more preferably 0.008 or more, and still more preferably 0.010 or more, from the viewpoint of suppressing coalescence of bubbles in the gas discharge portion of the sparger, suppressing an increase in bubble diameter, and easily increasing kLa.

Further, the A/X may be 0.1 or less, is preferably 0.05 or less, more preferably 0.03 or less, and still more preferably 0.025 or less, from the viewpoint of suppressing the ununiform ejection of bubbles, increasing kLa, and easily suppressing the damage to cells.

In addition, the X may be set depending on the kind of the cell to be cultured and the purpose of the culture; however, the X may be 0.5 $m^3$ or more, preferably 1.0 $m^3$ or more, and more preferably 1.1 $m^3$ or more, from the viewpoint of easily increasing the amount of the product obtained in a case where the cell culture method according to the present disclosure is used for the product producing method or from the viewpoint of easily obtaining a large number of cells.

The upper limit of the X is not particularly limited, but for example, may be 10 $m^3$ or less.

Flow Rate of Gas and Volume of Cell Suspension

In the culture, the flow rate Q ($m^3$/min) of the gas discharged from the sparger and the volume X ($m^3$) of the cell suspension in the culture vessel satisfy Expression 1-3.

$$0.001 \leq Q/X \leq 0.1 \qquad \text{Expression 1-3}$$

In a case where the culture vessel includes a plurality of spargers, the flow rate Q of the gas refers to the total value of the flow rates of the gas in all the spargers.

The Q/X may be 0.001 or more, is preferably 0.003 or more, more preferably 0.005 or more, and still more preferably 0.01 or more, from the viewpoint that oxygen necessary for cell culture is sufficiently supplied to the cell suspension and the cell concentration is easily increased.

Further, the Q/X may be 0.1 or less, is preferably 0.07 or less, more preferably 0.05 or less, and still more preferably 0.03 or less, from the viewpoint of easily suppressing the damage to cells.

Volume Average Bubble Diameter Dv of Bubbles

In a case where the cell suspension in the culture vessel is replaced with a measurement solution which is pure water containing 1 g/L of poloxamer 188, 7 g/L of sodium chloride, and 2 g/L of sodium hydrogen carbonate, an air gas having the same flow rate as that of the gas including 30% by mass of oxygen discharged from the sparger in the culture is sent from the sparger to the measurement solution, and a bubble diameter distribution in a gas discharge outlet of the sparger is measured, a volume average bubble diameter Dv (μm) of bubbles of the air gas preferably satisfies Expression 2-1.

$$50 \leq Dv \leq 800. \qquad \text{Expression 2-1}$$

Further, since it is difficult to measure the bubble diameter distribution of bubbles and the final speed of bubbles in case of using the cell suspension, in the present disclosure, the bubble diameter distribution of bubbles, the final speed of bubbles, or the like is determined by the value measured using the measurement solution.

The Dv is preferably 50 μm or more, more preferably 80 μm or more, and still more preferably 100 μm or more, from the viewpoint of suppressing the damage to cells.

In addition, the Dv is preferably 800 μm or less, more preferably 600 μm or less, still more preferably 500 μm or less, and particularly preferably 400 μm or less, from the viewpoint of increasing kLa to enable cell culture at a high cell concentration.

The detailed measuring method of the bubble diameter distribution (cumulative volume distribution) is as follows.

As a measuring device, FBRM® Particle Track™ G400 manufactured by Mettler-Toledo International Inc. is used.

A bubble diameter sensor of FBRM® G 400 is inserted, from above the culture vessel, at a position 20 mm away from the sparger in the height direction (vertical direction) of the culture vessel, in which the cell suspension is replaced with the measurement solution, and the measurement is performed to obtain the bubble diameter distribution.

The volume of the measurement solution is the same as the liquid volume of the cell suspension in the culture.

As the measurement conditions, the number-based measurement mode is used, and the measurement is performed with a sampling interval of 10 seconds and a migration average of 20 points. In addition, the Stuck Particle Correction function was activated to eliminate the detection of fixed points on the surface of the measurement lens. The measurement range is 1 μm to 4,000 μm, and the measurement section is divided into 200 intervals as the data interval on a logarithmic basis. At this time, in a case where the measured diameter of the next section is D(n+1) with respect to the measured diameter D(n) of the n-th section, Equation A is established.

$$D(n+1)=1.042D(n) \qquad \text{Equation A}$$

Using this setting condition, the BLANK data under the condition of an aeration flow rate of zero and the data during aeration are measured. In a case where the frequency of the measured data during aeration in a data section D(n) is denoted by f(n), and the frequency of the BLANK data in a data section D(n) is denoted by f0(n), the treatment described in Expression B is performed to obtain the BLANK treated data g(n).

$$g(n)=f(n)-f0(n) \qquad \text{Equation B}$$

Next, the number-based measured data is converted into volume-based measure data V(n) by performing the calculation described in Equation C.

$$V(n) = \tfrac{1}{6}\pi D(n)^3 g(n) \qquad \text{Equation C}$$

Further, the volume average diameter Dv is obtained by performing the calculation described in Equation D.

$$D_V = \frac{\sum \{V(n)D(n)\}}{\sum V(n)} \qquad \text{Equation D}$$

The volume-based cumulative distribution G(n) is obtained accordings to Eauation E.

$$G(n) = \sum_{i=1}^{n} V(i) \qquad \text{Equation E}$$

The cumulative volume distribution can be obtained using the above equation.

Bubble Diameter Distribution

In the bubble diameter distribution, a proportion of the cumulative volume of the air bubbles having a bubble diameter of 20 μm or more and 500 μm or less is preferably 30% by volume or more of the total volume of the bubbles in the bubble diameter distribution, from the viewpoint of suppressing cell damage.

The proportion of the cumulative volume of the air bubbles is obtained using Equation E by dividing the value, which is obtained by subtracting the cumulative volume of the air bubbles having a bubble diameter of less than 20 μm from the cumulative volume of the air bubbles having a bubble diameter of 500 μm or less, by the total volume of the bubbles.

The proportion of the cumulative volume is preferably 30% by volume or more, preferably 50% by volume or more, more preferably 70% by volume or more, and still more preferably 90% by volume or more, from the viewpoint of suppressing cell damage.

The upper limit value of the proportion of the cumulative volume is not particularly limited; however, it may be, for example, 100% by volume or less.

Oxygen Transfer Capacity Coefficient kLa

The oxygen transfer capacity coefficient kLa at the time of culturing is preferably 15 hr$^{-1}$ or more from the viewpoint of increasing the concentration of cultured cells and easily suppressing the damage to cells.

Further, the kLa is more preferably 15 hr$^{-1}$ or more, still more preferably 20 hr$^{-1}$ or more, particularly preferably 25 hr$^{-1}$ or more, and most preferably 30 hr$^{-1}$ or more, from the viewpoint of increasing the concentration of cultured cells and easily suppressing the damage to cells.

The upper limit value of the kLa is not particularly limited; however, it may be, for example, 100 hr$^{-1}$ or less.

The kLa can be measured by the method described in (1) to (4) below.

<<(1) Preparation of Solution>>

According to the same method as the method in the measurement of the bubble diameter distribution, a culture vessel in which the cell suspension in the culture vessel is replaced with the measurement solution is prepared.

<<(2) Preparation of Oxygen Concentration Sensor>>

As the oxygen concentration sensor, InPro® 6800/12/220 manufactured by Mettler-Toledo International Inc. is used. A membrane, O2 Membrane body T-96 manufactured by Mettler-Toledo International Inc., is inserted inside the sensor, and further, an O2 electrolyte, O2-Electrolyte manufactured by Mettler-Toledo International Inc., is enclosed therein.

As the oxygen concentration indication meter, M400 Type 3 manufactured by Mettler-Toledo International Inc. is used.

Zero oxygen tables for InLab sensors (sodium sulfite tablet) manufactured by Mettler-Toledo International Inc. is dissolved in 40 mL of pure water, followed by waiting for 5 minutes.

The oxygen concentration sensor is put in the solution and allowed to be left for 20 minutes. After 5 minutes, a zero-point calibration of the oxygen concentration sensor is performed.

Assuming that the height of the oxygen concentration sensor is 0% at the center of the measurement solution in the height direction, the height of the liquid surface of the measurement solution is 100%, and the height of the solution bottom surface of the measurement solution is −100%, the oxygen concentration sensor is inserted to at a position of a height −100% to 0%.

The measurement solution is kept warm at 37° C.

While stirring, aeration is performed by Air from a sparger having a hole diameter of 20 μm, at 0.02 vvm for 24 hours. In the present disclosure, "vvm" represents the fold of the volume used for aeration per 1 minute with respect to the liquid volume.

(In a case where the liquid can be saturated with Air, the sparger hole diameter and flow rate do not matter).

When the aeration is completed, calibration is performed by setting Air as 100%.

<<(3) Oxygen Degassing>>

The measurement solution is kept warm at 37° C.

N$_2$ is supplied from a sparger having a hole diameter of 20 μm to the measurement solution in the culture vessel (for example, 0.02 vvm).

Waiting is performed until the oxygen concentration falls below 3%.

When the oxygen concentration is 3% or less, the supply of N$_2$ is stopped, and stirring is stopped.

In a case where the volume of the solution-free portion in the upper space of the culture vessel is denoted by V (L), Air is supplied to the upper space of the culture vessel at a flow rate of V/3 (L/min) for 15 minutes to replace N$_2$ in the upper space with Air. (In a case where five times the V can be replaced with Air, the flow rate and time do not matter.)

<<(4) Measurement>>

When the replacement is completed, a predetermined stirring condition and a predetermined gas aeration condition are set, and the oxygen concentration is measured. Air is used as the gas. The values represented by Expression KL are plotted on the vertical axis together with the time (h) on the lateral axis. The oxygen concentration is calculated from the slope of the graph in a range in which the oxygen concentration in the solution is 20% to 80% of the saturated oxygen concentration in a case where the Air is aerated.

$$\ln((C^*-C)/(C^*-C_0)) \qquad \text{Expression KL}$$

In the above formula, ln represents the natural logarithm, C* represents the saturated oxygen concentration, C$_0$ represents the oxygen concentration at the starting time of measurement, and C represents the measured oxygen concentration.

In addition, kLa may be calculated with reference to the content described in "DECHEMA Biotechnologie Recommendations for process engineering characterization of single-use bioreactors and mixing systems by using experimental methods, Publication date: January 2016".

Gas Discharge Speed

In the culture process, in a case where an air gas having the same flow rate Q (m³/min) of the gas including 30% by volume of oxygen discharged from the sparger in the culture is sent from the sparger to the measurement solution, and a bubble diameter distribution in a gas discharge outlet of the sparger is measured, the Q (m³/min), the A (m²), a density $\rho L$ (kg/m³) of the measurement solution, a density $\rho g$ (kg/m³) of the air gas, a viscosity $\mu L$ (kg/m/s) of the measurement solution, and a gravitational acceleration g (m/s²) preferably satisfy Expression 3-1.

$$0.1<(Q/A/60)/[\{3\times10^{-8}\times(\rho L-\rho g)\times g\}/(18\times\mu L)\}]<5 \quad \text{Expression 3-1}$$

Here, (Q/A/60) in Expression 3-1 represents the discharge speed of the gas, and $\{3\times10^{-8}\times(\rho L-\rho g)\times g\}/(18\times\mu L)\}$ represents the final speed of bubbles in the measurement solution in a case where the volume average bubble diameter Dv is 175 μm.

That is, Expression 3-1 represents that the ratio of the discharge speed of the gas to the final speed of the bubbles (the discharge speed of the gas/the final speed of the bubbles, also referred to as "ratio A") is 0.1 or more and 5 or less.

In a case where the ratio A is 0.1 or more, it is speculated that kLa is easily increased, and the damage to cells is easily suppressed since uniform pressure is easily applied to the sparger and ununiform discharge of bubbles from the gas discharge portion of the sparger is suppressed.

On the other hand, in a case where the ratio A is 5 or less, it is speculated to suppress that a next bubble is discharged before the bubble which has been discharged from the sparger rises in the solution and thus the bubbles aggregate and coalesce at the sparger exit.

Accordingly, it is speculated that the occurrence of events such as an increase in bubble diameter and ununiform bubble diameter distribution is reduced, kLa is easily increased, and the concentration of cultured cells is easily increased.

The ratio A is preferably 0.1 or more, more preferably 0.2 or more, still more preferably 0.4 or more, and most preferably 0.5 or more, from the viewpoint of easily increasing the concentration of cultured cells and easily suppressing the damage to cells.

Further, the ratio A is preferably 5 or less, more preferably 4 or less, still more preferably 3 or less, and most preferably 2 or less, from the viewpoint of easily increasing the concentration of cultured cells.

At the time of culturing, the flow rate Q (m³/min) of the gas discharged from the sparger and the A (m²) preferably satisfy Expression 4-1.

$$0.1 \leq Q/A \leq 5 \quad \text{Expression 4-1}$$

Q/A represents the gas discharge speed (m/min) as described above.

In a case where the Q/A is 0.1 m/min or more, since uniform pressure is easily applied to the sparger and ununiform discharge of bubbles from the gas discharge portion of the sparger is suppressed, kLa is easily increased, and it is speculated that the damage to cells is easily suppressed.

In a case where the Q/A is 5 m/min or less, it is speculated to suppress that the bubbles aggregate and coalesce at the sparger exit. Accordingly, it is speculated that the occurrence of events such as an increase in bubble diameter and ununiform bubble diameter distribution is reduced, kLa is easily increased, and the concentration of cultured cells is easily increased.

The Q/A is preferably 0.1 or more, more preferably 0.2 or more, still more preferably 0.4 or more, and most preferably 0.5 or more, from the viewpoint of easily increasing the concentration of cultured cells and easily suppressing the damage to cells.

Further, the Q/A is preferably 5 or less, more preferably 4 or less, still more preferably 3 or less, and most preferably 2 or less, from the viewpoint of easily increasing the concentration of cultured cells.

Retention Time

A liquid level ZL (m) from an inner bottom surface of the culture vessel to an upper surface of the cell suspension in the culture, a height Zs (m) from the inner bottom surface of the culture vessel to a sparger installation surface, a volume average bubble diameter Dv of bubbles in the bubble diameter distribution, a density $\rho L$ (kg/m³) of the measurement solution, a density $\rho g$ (kg/m³) of the air gas, a gravitational acceleration g (m/s²), and a viscosity $\mu L$ (kg/m/s) of the measurement solution preferably satisfy Expression 5-1.

$$2 \leq (ZL-Zs)/\{Dv^2\times10^{-12}\times(\rho L-\rho g)\times g/(18\times\mu L)\} \leq 300 \quad \text{Expression 5-1}$$

Here, the height Zs (m) refers to the distance from the inner bottom surface of the culture vessel to the uppermost part of the gas supply portion of the sparger.

In Expression 5-1, (ZL–Zs) represents the distance migrated until the bubbles discharged from the sparger reach the liquid surface.

In addition, in Expression 5-1, $\{Dv^2\times10^{-12}\times(\rho L-\rho g)\times g\}/(18\times\mu L)\}$ represents the final speed of bubbles having the volume average bubble diameter Dv in the measurement solution.

That is, Expression 5-1 represents the retention time (s) of the bubble in the measurement solution, which is a value obtained by dividing the migration distance of a bubble by the final speed of the bubble.

In a case where the retention time is 2 seconds or more, it is speculated that the amount of oxygen supplied from bubbles is increased, kLa is easily increased, and the concentration of cultured cells at the time of culturing is easily increased.

Further, in a case where the retention time is 300 seconds or less, it is speculated that the damage to cells is easily suppressed.

The retention time is preferably 2 seconds or more, more preferably 15 seconds or more, still more preferably 30 seconds or more, and particularly preferably 40 seconds or more, from the viewpoint of easily increasing kLa and easily increasing the concentration of cultured cells at the time of culturing.

The retention time is preferably 300 seconds or less, more preferably 200 seconds or less, still more preferably 150 seconds or less, and particularly preferably 120 seconds or less, from the viewpoint of easily suppressing the damage to cells.

Shape of Culture Vessel

The X (m³), the ZL (m), and the Zs (m) preferably satisfy at least one selected from the group consisting of Expression 6-1 and Expression 6-2 and more preferably satisfy both.

$$Zs/ZL \leq 0.5 \quad \text{Expression 6-1}$$

$$0.5 \leq ZL/(4\times X/ZL/3.14)^{0.5} \leq 4 \quad \text{Expression 6-2}$$

Zs/ZL in Expression 6-1 is a ratio of the liquid level ZL (m) from the inner bottom surface of the culture vessel to the upper surface of the cell suspension, to the height Zs (m) from the inner bottom surface of the culture vessel to the sparger installation surface. In a case where the ratio is 0.5 or less, the sparger is installed at a position below the center of the height from the inner bottom surface to the liquid surface in the height direction in the culture vessel.

It is speculated that kLa is easily increased and the cell concentration at the time of culturing is easily increased since the lower position of the sparger gives the longer retention time of the bubbles discharged from the sparger.

The Zs/ZL is preferably 0.5 or less, more preferably 0.3 or less, still more preferably 0.2 or less, and particularly preferably 0.1 or less, from the viewpoint of easily increasing the cell concentration at the time of culturing.

The lower limit of Zs/ZL is not particularly limited, and an aspect (Zs/ZL=0) in which a sparger is formed on the bottom surface may be adopted.

$(4 \times X/ZL/3.14)^{0.5}$ in Expression 6-2 represents an equivalent circle diameter in a plane horizontal to the bottom surface of the culture vessel, in a case of assuming that the inner diameter of the culture vessel does not change due to the change in the height direction.

That is, $(4 \times X/ZL/3.14)^{0.5}$ in Expression 6-2 represents a value of the ratio of the height of the liquid surface of the cell suspension in the culture vessel to the equivalent circle diameter (the height of the liquid surface/the equivalent circle diameter, also referred to as "ratio B").

In a case where the ratio B is 0.5 seconds or more, it is speculated that the retention time of bubbles is increased, kLa is easily increased, and the concentration of cultured cells at the time of culturing is easily increased.

In a case where the ratio B is 4 or less, it is speculated that the oxygen concentration is easily made to be homogeneous in the culture vessel and a bottom area sufficient for disposing a sparger having the necessary area (the surface area A) is easily secured.

The ratio B is preferably 0.5 or more, more preferably 0.8 or more, still more preferably 1.0 or more, and particularly preferably 1.2 or more, from the viewpoint of increasing the retention time of the bubble, easily increasing kLa, and easily increasing the concentration of cultured cells at the time of culturing.

Further, the ratio B is preferably 4 or less, more preferably 3 or less, still more preferably 2.5 or less, and particularly preferably 2 or less, from the viewpoint of easily homogenizing the oxygen concentration in the culture vessel and easily securing a bottom area sufficient for disposing a sparger having the necessary area (the surface area A).

[Stirring Member]

The culture vessel in the present disclosure may further include a stirring member.

In a case where the culture vessel is stirred by the stirring member, it is speculated that the bubbles discharged from the sparger are also stirred, kLa is easily increased, and the cell concentration at which cell culture is possible is easily increased.

The stirring member is not particularly limited, and a stirring member used in a known sparger can be used, and examples thereof include a stirrer having a stirring blade.

The position of the stirrer having a stirring blade, the size of the stirring blade, and the like are not particularly limited and may be designed depending on the cell kind to be used, the volume of cell suspension, the amount of oxygen to be supplied, or the position, number, size, or the like of the sparger. Further, in order to quickly stir bubbles coming out of the sparger and suppress coalescence of the bubbles, it is preferable to dispose a stirring member at a position close to the sparger.

As a method using other than the stirrer having a stirring blade, for example, a method of shaking the culture vessel or a method of circulating the cell suspension in the culture vessel with a pump or the like can be mentioned.

[Cells]

Cells to be cultured in the cell culture method according to the present disclosure are not particularly limited, and examples thereof include animal cells, plant cells, eukaryotic cells such as yeast, and prokaryotic cells such as *Bacillus subtilis* and *Escherichia coli*. The cells may be ES cells, iPS cells, various stem cells, or the like.

The cells to be cultured in the cell culture method according to the present disclosure may be cells that produce a product. In a case where cells that produce a product are cultured, the product is produced by the cells, and in a case where the product is collected, the substance production using the cells can be performed.

That is, one preferred aspect according to the present disclosure is a product producing method including culturing cells with the cell culture method according to the present disclosure and obtaining a product produced by the cultured cells.

The cells used cells for producing a product are not particularly limited and may be any ones of animal cells, plant cells, insect cells, eukaryotic cells such as yeast, or prokaryotic cells such as *Bacillus subtilis* and *Escherichia coli*. Animal cells such as CHO cells, BHK-21 cells, C127 cells, NSO cells, and SP2/0-Ag14 cells are preferable, and CHO cells are more preferable in that many analyzes have been carried out and genetic engineering techniques have been established. Even in a case where the cells do not originally produce the desired product or the production amount is small, the desired product can be efficiently produced, for example, by introducing an expression vector, such as a plasmid, encoding a protein required for producing the product into the cell. The product produced by the cells in the present disclosure is not particularly limited as long as it is a substance produced by the cells in a cell suspension, and examples thereof include alcohols, enzymes, antibiotics, nucleic acids, recombinant proteins, and antibodies. Among them, the product is preferably a recombinant protein or an antibody and more preferably an antibody.

The method for obtaining the product is not particularly limited, and a known method can be used.

In a case where an antibody is produced in animal cells, the kind of antibody is not particularly limited, and examples thereof include anti-IL-6 receptor antibody, anti-IL-6 antibody, anti-glypican-3 antibody, anti-CD3 antibody, anti-CD20 antibody, anti-GPIIb/IIIa antibody, anti-TNF antibody, anti-CD25 antibody, anti-EGFR antibody, anti-Her2/neu antibody, anti-RSV antibody, anti-CD33 antibody, anti-CD52 antibody, anti-IgE antibody, anti-CD11a antibody, anti-VEGF antibody, and anti-VLA4 antibody. Examples of antibodies to be produced include not only monoclonal antibodies derived from animals such as human, mouse, rat, hamster, rabbit, and monkeys, but also artificially modified antibodies such as chimeric antibodies, humanized antibodies, and bispecific antibodies.

The concentration of cells in the cell suspension contained in the culture vessel is not particularly limited and may be determined in consideration of the cell kind and the like.

However, since the higher concentration of cells in the cell suspension contained in the culture vessel gives the larger number of cells and the larger production amount of a product in a case where the cells produce the product, it is preferable that the cell concentration is high.

From these facts, the concentration of cells in the cell suspension contained in the culture vessel is preferably $4 \times 10^7$ cells/mL or more, more preferably $5 \times 10^7$ cells/mL or more, and still more preferably $6 \times 10^7$ cells/mL.

The upper limit of the cell concentration is not particularly limited, but for example, $30 \times 10^7$ cells/mL or less is preferable from the viewpoint of improving the cell survival rate.

As a medium used for cell culture, a liquid medium usually used for cell culture can be used. For example, OptiCHO™ (Thermo Fisher Scientific, Inc., 12681011) medium, Dulbecco's modified Eagle medium (DMEM), Eagle minimum essential medium (MEM), RPMI-1640 medium, RPMI-1641 medium, F-12K medium, Ham's F12 medium, Iscove's modified Dulbecco's medium (IMDM), McCoy's 5A medium, Leibovitz's L-15 medium, and EX-CELL (trade mark) 300 series (JRH Biosciences), CHO-S-SFMII (Invitrogen), CHO-SF (Sigma-Aldrich Co. LLC), CD-CHO (Invitrogen), ISCHO-V (FUJIFILM Irvine Scientific), PF-ACF-CHO (Sigma-Aldrich Co. LLC), and the like can be used.

Serum such as fetal calf serum (FCS) may be added to the medium. Alternatively, the medium may be serum-free medium such as a fully synthetic medium.

The medium may be supplemented with additional components such as amino acids, salts, sugars, vitamins, hormones, growth factors, buffers, antibiotics, lipids, trace elements, and hydrolysates of plant proteins.

Although the pH of the medium varies depending on the cells to be cultured, the medium is generally pH 6.0 to 8.0, preferably pH 6.8 to 7.6, and more preferably pH 7.0 to 7.4.

The culture temperature is generally 30° C. to 40° C., preferably 32° C. to 37° C., and more preferably 36° C. to 37° C., and the culture temperature may be changed during the culture.

The culture may be performed in an atmosphere having a $CO_2$ concentration of 0% by volume to 40% by volume and preferably in an atmosphere having a $CO_2$ concentration of 2% by volume to 10% by volume.

In the culture, the medium can be replaced, aerated, and stirred as necessary.

[Perfusion Culture]

The cell culture is preferably a perfusion culture. The perfusion culture is a culture method in which fresh medium is added and at the same time used medium is removed. In a case of using the perfusion culture, it is also possible to achieve a high cell concentration exceeding $1 \times 10^8$ cells/mL. A typical perfusion culture begins with a batch culture start-up lasting 1 or 2 days, thereafter a fresh supplying culture medium is added to the culture continuously, stepwise, and/or intermittently, and the used medium is removed at the same time. In the perfusion culture, methods such as sedimentation, centrifugation, and filtration can be used to remove the used medium while maintaining the cell concentration. Perfusion may be continuous, stepwise, or intermittent, or a combination thereof. The number of days of the perfusion culture is preferably 5 days to 150 days, more preferably 10 days to 100 days, and still more preferably 20 days to 80 days. It is preferable for the number of days of the perfusion culture to be 5 days or more since the obtained cell number is large and the production amount of a product is large in a case where the cells produce the product. It is preferable for the number of days of the perfusion culture to be 150 days or less from the viewpoint of preventing clogging of the filtration membrane used in the perfusion culture and preventing contamination.

The perfusion culture can be performed using, for example, a perfusion cell culture device described later.

Extraction of the cell suspension from the culture vessel can usually be performed using a pump, but other available liquid feeding units may be used. The cell suspension extracted from the culture vessel is subjected to treatments such as product collection and removal of the dead cells. The cell suspension extracted from the culture vessel may be partially discarded or returned to the culture vessel after treatments such as product collection and removal of the dead cells.

In a case where a loss of the medium occurs due to the above treatments, the loss can be compensated, for example, by supplying a fresh medium to the culture vessel.

(Product Producing Method)

The product producing method according to the present disclosure includes:

culturing cells by the cell culture method according to the present disclosure (hereinafter, also referred to as "cell culture process"); and obtaining a product produced by the cultured cells (hereinafter, also referred to as "product collecting process").

In the product producing method according to the present disclosure, since the cell culture method according to the present disclosure is used for culturing, it is speculated that cells are cultured at a high cell concentration and damage to the cells is suppressed. Accordingly, it is speculated that the production amount of the product increased and the quality of the product can be improved.

<Cell Culture Process>

The cell culture process is the same as the cell culture process in the above-described cell culture method according to the present disclosure.

As the cells producing a product, the cells producing a product exemplified above can be used, and as the products, the product exemplified above can be produced. The product is preferably an antibody.

<Product Collecting Process>

As the product collection in the product collecting process, the cell suspension may be simply collected. For example, a liquid obtained by removing at least a part of the cells from the cell suspension using a filter or a centrifuge may be collected, and a known method is used without particular limitation. In a case of desiring to improve the purity of the product, change the solvent of the product, or change the form of the product to, for example, a power form, the cell suspension or the liquid can be subjected to further treatment.

Further, in a case where the cell culture is performed by the above-described perfusion culture, a part of the cell suspension can be collected while being perfused, or a part of the cell suspension can be collected as a liquid which is obtained by removing at least a part of cells from the part of cell suspension, which is filtered or centrifuged while being perfused.

For example, the product can be purified by a purification treatment. The obtained product can be purified to high purity. In a case where the product is a polypeptide such as an antibody or a fragment thereof, the separation and purification of the product may be carried out by using the ordinary separation and purification method used for a polypeptide. For example, a chromatography column for affinity chromatography or the like, a filter, ultrafiltration, salting out, dialysis, SDS polyacrylamide gel electrophoresis, and isoelectric focusing electrophoresis can be appropriately selected and combined to separate and purify a polypeptide; however, the present invention is not limited to thereof. The concentration of the obtained polypeptide can be measured by measuring the absorbance or by an enzyme-linked immunosorbent assay (ELISA).

In the cell culture device according to the present disclosure, a culture vessel which contains a cell suspension containing cells and a sparger for discharging a gas including 30% by volume or more of oxygen into the cell suspension in the cell culture vessel are provided, an average hole diameter of the sparger is 1 μm or more and 300 μm or less, and a surface area A (m$^2$) of the sparger, a volume Xmax (m$^3$) of the cell suspension with which the culture vessel can be maximally filled satisfy Expression 7-1 and Expression 7-2.

$$0.004 \leq A/Xmax \leq 0.1 \qquad \text{Expression 7-1}$$

$$Xmax \geq 0.5 \qquad \text{Expression 7-2}$$

The respective constituent elements such as the culture vessel and the sparger in the cell culture device according to the present disclosure have the same meanings as the respective constituent elements in the above-described cell culture method according to the present disclosure, and the same applies for the preferred aspects.

Further, in the preferred aspect of the cell culture device according to the present disclosure, X in the cell culture method according to the present disclosure is to be read as Xmax described later.

Hereinafter, points that are not described in the cell culture method according to the present disclosure will be described.

Xmax is, for example, the maximum value of the volume of cell suspension generally used in the cell culture device, and the maximum value of the usable volume of the cell suspension in the catalog of the cell culture device is determined as Xmax.

In a case where a usable volume of the cell suspension is not particularly determined in the cell culture device, the usable volume can be determined in consideration of the embodiment, for example, 80% by volume of the capacity of the culture vessel.

Here, the A/Xmax is preferably 0.004 or more, more preferably 0.006 or more, still more preferably 0.008 or more, and particularly preferably 0.01 or more, from the viewpoint of suppressing coalescence of bubbles in the gas discharge portion of the sparger, suppressing an increase in bubble diameter, and easily increasing kLa.

Further, the A/Xmax is preferably 0.1 or less, more preferably 0.05 or less, still more preferably 0.03 or less, and particularly preferably 0.025 or less, from the viewpoint of suppressing the ununiform ejection of bubbles, increasing kLa, and easily suppressing the damage to cells.

In addition, the Xmax is set depending on the kind of cell to be cultured and the purpose of the culture; however, the X is preferably 0.5 m$^3$ or more, more preferably 1.0 m$^3$ or more, and still more preferably 1.1 m$^3$ or more, from the viewpoint of easily increasing the amount of the product obtained in a case where the cell culture method according to the present disclosure is used for the product producing method or from the viewpoint of easily obtaining a large number of cells.

The upper limit of the Xmax is not particularly limited, but for example, may be 10 m$^3$ or less.

In the cell culture device according to the present disclosure, it is preferable that a liquid level ZLmax (m) from an inner bottom surface of the culture vessel to an upper surface of the cell suspension in a case where the culture vessel is maximally filled with the cell suspension, and a height Zs (m) from the inner bottom surface of the culture vessel to a sparger installation surface satisfy Expression 8-1.

$$2 \leq (ZLmax - Zs)/0.02 \leq 300 \qquad \text{Expression 8-1}$$

The ZLmax−Zs represents the distance from the liquid surface of the cell suspension to the sparger ground surface in a case where the culture vessel is maximally filled with the cell suspension.

In a case where the (ZLmax−Zs)/0.02 is 2 or more, it is speculated that kLa is easily increased and the cell concentration at the time of culturing is easily increased since the retention time of the bubbles discharged from the sparger is long.

Further, in a case where the (ZLmax−Zs)/0.02 is 300 or less, it is speculated that the damage to cells is easily suppressed since the retention time of the bubbles is not too long.

The (ZLmax−Zs)/0.02 is preferably 2 or more, more preferably 15 or more, still more preferably 30 or more, and most preferably 40 or more, from the viewpoint of easily increasing the cell concentration cells at the time of culturing.

Further, the (ZLmax−Zs)/0.02 is preferably 300 or less, more preferably 200 or less, still more preferably 150 or less, and most preferably 120 or less, from the viewpoint of easily suppressing the damage to cells.

In the cell culture device according to the present disclosure, it is preferable that Xmax (m$^3$), ZLmax (m), and Zs (m) satisfy Expression 9-1 and Expression 9-2.

$$Zs/ZLmax \leq 0.5 \qquad \text{Expression 9-1}$$

$$0.5 < ZLmax/\{(4 \times Xmax/ZLmax/3.14)^{0.5}\} \leq 4 \qquad \text{Expression 9-2}$$

Zs/ZLmax in Expression 9-1 is a ratio of the liquid level ZL (m) from the inner bottom surface of the culture vessel to the upper surface of the cell suspension in a case where the culture vessel is maximally filled with the cell suspension, to the height Zs (m) from the inner bottom surface of the culture vessel to the sparger installation surface. In a case where the ratio is 0.5 or less, the sparger is installed at a position below the center of the height from the inner bottom surface to the liquid surface in the height direction in the culture vessel in a case where the culture vessel is maximally filled with the cell suspension.

It is speculated that kLa is easily increased and the cell concentration at the time of culturing is easily increased since the lower position of the sparger gives the longer retention time of the bubbles discharged from the sparger.

The Zs/ZLmax is preferably 0.5 or less, preferably 0.3 or less, more preferably 0.2 or less, and still more preferably 0.1 or less, from the viewpoint of easily increasing the cell concentration at the time of culturing.

The lower limit of Zs/ZL is not particularly limited, and an aspect (Zs/ZLmax=0) in which a sparger is formed on the bottom surface may be adopted.

$(4 \times Xmax/ZLmax/3.14)^{0.5}$ in Expression 9-2 represents a equivalent circle diameter in a plane horizontal to the bottom surface of the culture vessel, in a case of assuming that the inner diameter of the culture vessel does not change due to the change in the height direction.

That is, $ZLmax/\{(4 \times Xmax/ZLmax/3.14)^{0.5}\}$ in Expression 9-2 represents a value of the ratio of the height of the liquid surface of the cell suspension in the culture vessel in a case where the culture vessel is maximally filled with the cell suspension to the equivalent circle diameter (the height of the liquid surface/the equivalent circle diameter, also referred to as "ratio C").

In a case where the ratio C is 0.5 seconds or more, it is speculated that the retention time of bubbles is increased, kLa is easily increased, and the cell concentration at the time of culturing is easily increased.

In a case where the ratio C is 4 or less, it is speculated that the oxygen concentration is easily made to be homogeneous in the culture vessel and a bottom area sufficient for disposing a sparger having the necessary area (the surface area A) is easily secured.

The ratio C is preferably 0.5 or more, preferably 0.8 or more, more preferably 1.0 or more, and still more preferably 1.2 or more, from the viewpoint of increasing the retention time of the bubble, easily increasing kLa, and easily increasing the cell concentration at the time of culturing.

Further, the ratio C is preferably 4 or less, preferably 3 or less, more preferably 2.5 or less, and still more preferably 2 or less, from the viewpoint of easily homogenizing the oxygen concentration in the culture vessel and easily securing a bottom area sufficient for disposing a sparger having the necessary area.

The cell culture device described in the present disclosure is preferably a perfusion cell culture device.

The perfusion cell culture device is not particularly limited as long as it is a device that can realize the perfusion culture described above and can have a known design.

Figure 3:
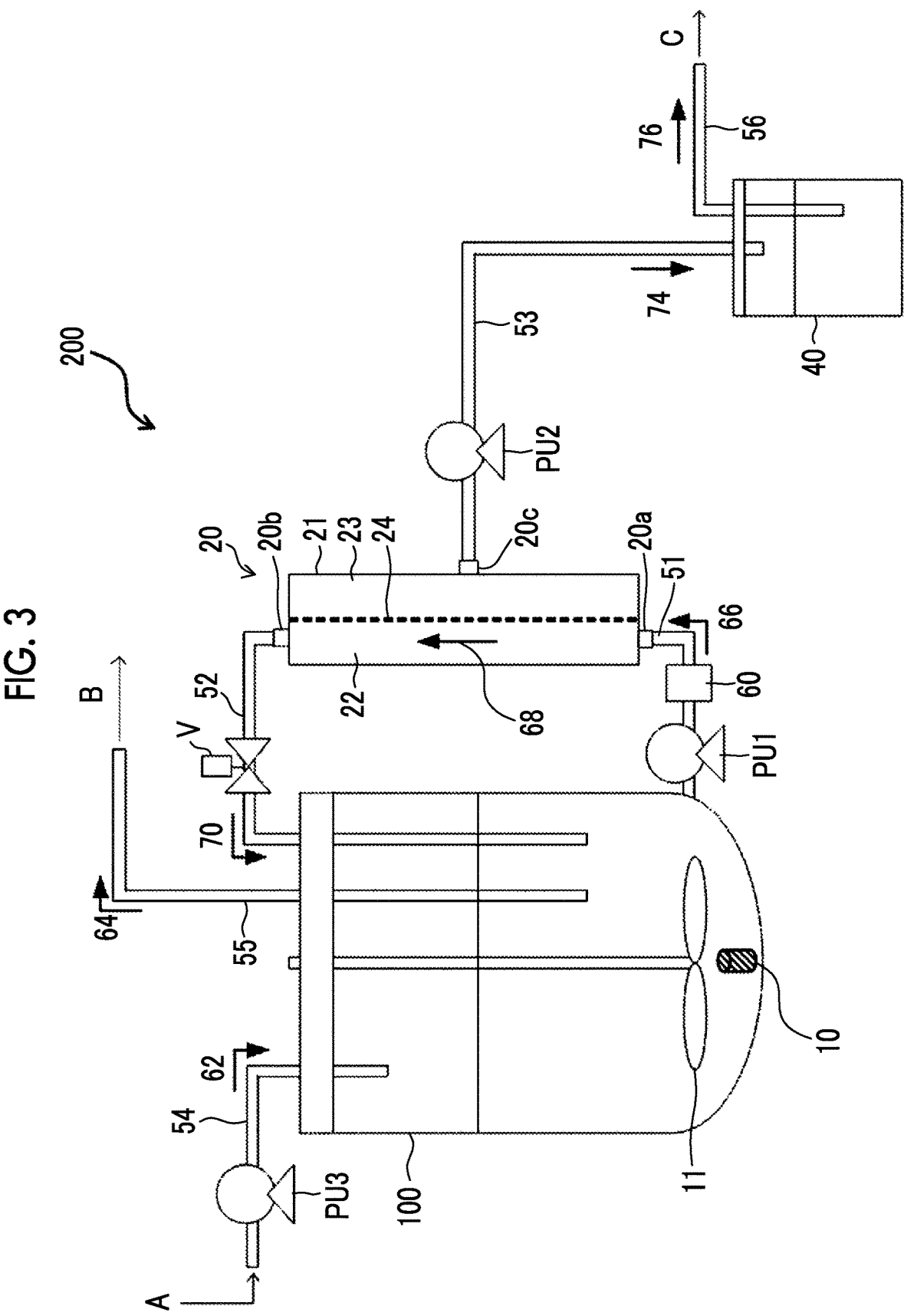
FIG. 3 is a schematic configuration diagram illustrating an example of a configuration of a cell culture device applicable to the implementation of the product producing method according to the present disclosure.

One example of the cell culture method, the product producing method, and the cell culture device according to the present disclosure will be collectively described with reference to FIG. 3. FIG. 3 is a schematic configuration diagram illustrating an example of a configuration of a cell culture device 200 applicable to the implementation of the product producing method according to the present disclosure.

In FIG. 3, the cell culture device 200 includes the culture vessel 100 containing a cell suspension, a filter unit 20 having a filter membrane 24 that performs a membrane separation treatment on the cell suspension extracted from the culture vessel 100, a flow channel 52 for returning the components blocked by the filter membrane 24 to the culture vessel 100, a flow channel 53 for passing the components that have permeated through the filter membrane 24, and a collection tank 40 connected to the flow channel 53.

A stirring device having a stirring blade 11 and a sparger 10 are provided inside the culture vessel 100. In a case where the stirring blade 11 is rotated, the medium contained in the culture vessel 100 is stirred, and thus the homogeneity of the medium is maintained. Further, kLa is easily increased by stirring the bubbles discharged from the sparger 10.

The number, position, and the like of the sparger 10 can be the same as those described in the above-described cell culture method according to the present disclosure.

The flow channel 51 has one end connected to the bottom of the culture vessel 100 and the other end connected to an inlet 20a of the filter unit 20. An arrow 66 indicates the flowing direction of the cell suspension in the flow channel 51. A pump PU1 for extracting the cell suspension contained in the culture vessel 100 and sending the extracted cell suspension to the filter unit 20 is provided in the middle of the flow channel 51. As the pump PU1, for example, a magnetic levitation type pump can be used. The liquid sending pressure can be measured by a pressure gauge 60 installed between the pump PU1 and the filter unit 20. The liquid sending pressure of the pump PU1 can be adjusted by the opening degree of a pinch valve V provided on the flow channel 52. Further, the liquid sending flow rate can be adjusted by the rotation speed of the pump PU1.

In addition, a reciprocating pump can be used as the pump PU1. In a case where a reciprocating pump is used for PUT, it is not necessary to connect the one end of the flow channel 51 to the bottom of the culture vessel 100. Due to the reciprocation of PUT, the arrows 66, 68, and 70 are inverted with respect to FIG. 3, and the cell suspension is extracted from the culture vessel. In a case where the arrows 66, 68, and 70 are reverted in the direction illustrated in FIG. 3, the cell suspension is returned to the culture vessel.

The filter unit 20 includes a vessel 21 and a filter membrane 24 that divides the space inside the vessel 21 into a supply side 22 and a permeation side 23 and performs a membrane separation treatment on the cell suspension extracted from the culture vessel 100. An arrow 68 indicates the flowing direction of the cell suspension in the filter unit 20. Further, the filter unit 20 has, on the supply side 22, an inlet 20a into which the cell suspension flows in and an outlet 20b from which the cell suspension flows out. The cell suspension extracted from the culture vessel 100 passes through the filter membrane 24 while flowing into the inside of the vessel 21 through the inlet 20a and flowing out of the outside of the vessel 21 through the outlet 20b. The filter unit 20 performs the membrane separation treatment by a tangential flow type method in which a component having a small size is sent to the permeation side 23 while a target liquid for the membrane separation treatment flows along the membrane surface of the filter membrane 24 (in the direction parallel to the membrane surface). In the membrane separation treatment by a tangential flow type method, a flow in which the cell suspension extracted from the culture vessel 100 circulates in one direction in parallel along the membrane surface of the filter membrane 24 may be formed, or a flow in which the cell suspension reciprocates along the membrane surface of the filter membrane 24 may be formed. In a case of forming a circulating flow, a KrosFlo® perfusion culture flow path device (KML-100, KPS-200, KPS-600) manufactured by Spectrum Life-Sciences LLC, PuraLev® series manufactured by LEVIT-RONIX, or the like can be suitably used. In a case where forming a reciprocating flow, the ATF® system manufactured by REPLIGEN can be preferably used.

The cells contained in the cell suspension do not permeate through the filter membrane 24, flow out of the outside of the vessel 21 through the outlet 20b, and are returned to the inside of the culture vessel 100 through the flow channel 52. An arrow 70 indicates the flowing direction of the cell suspension in the flow channel 52. On the other hand, a product such as an antibody contained in the cell suspension permeates through the filter membrane 24 and is ejected to the outside of the vessel 21 through an ejection outlet 20c provided on the permeation side 23. The flow channel 53 having a pump PU2 is connected to the permeation side 23, and a permeated liquid including a product (for example, antibody) permeated into the permeation side 23 is collected at the collection tank 40 through the flow channel 53. An arrow 74 indicates the flowing direction of the permeated liquid in the flow channel 53. The pump PU2 may be a peristaltic pump or a magnetic levitation type pump.

As the filter membrane 24, it is possible to use a mesh filter formed by weaving a fibrous member in a mesh form. In a case of using the mesh filter, it is possible to promote the ejection of components unnecessary for cell culture, which includes dead cell bodies and cell debris, to the permeation side, as compared with a case of using a hollow fiber membrane. As a result, the components unnecessary for cell culture can be effectively removed from the culture vessel 100, and thus the proliferation of cells in the culture vessel 100 can be enhanced.

A hollow fiber membrane can be used as the filter membrane 24. In a case where the hollow fiber membrane is used, the risk of the cell permeation into the permeation side can be reduced as compared with a case of using the mesh filter. Further, it is possible to reduce the risk of clogging of the filter membrane 24, caused by entering of cells. Accordingly, cell loss can be reduced.

A product (for example, antibody) contained in the permeated liquid that has permeated through the filter membrane 24 and collected in the collection tank 40 is sent, through the flow channel 56, to a purification treatment portion (not illustrated in the figure) in which the purification of the product (for example, antibody) is performed. The collected permeated liquid may be stored for the moment in the collection tank 40 or may be directly sent to the purification treatment portion without being stored in the tank. In a case where being stored in the collection tank 40, the influence on the purification treatment portion can be minimized even in a case where the flow rate of the permeated liquid changes.

An arrow 76 indicates the direction in which the permeated liquid flows in the flow channel 56, and C indicates the migration of the permeated liquid used in the purification treatment.

The cell culture device 200 has a flow channel 54 for supplying a fresh medium to the culture vessel 100, and a pump PU3 provided in the middle of the flow channel 54. A indicates a fresh medium supply port, and an arrow 62 indicates the direction in which the cell suspension flows in the flow channel 54. The pump PU3 may be a peristaltic pump or a magnetic levitation type pump.

In order to prevent the concentration of cells in the culture vessel 100 from becoming excessively high, a cell bleeding treatment in which a part of the cells in the culture vessel 100 is extracted at an appropriate timing during the culture period is performed. In the cell bleeding treatment, the cells in the culture vessel 100 are ejected to the outside of the culture vessel 100 through the flow channel 55. An arrow 64 indicates the direction in which the cell suspension flows in the flow channel 55, and B indicates the migration of the cell suspension used in the cell bleeding treatment.

In the cell culture device 200 illustrated in FIG. 3, the separation treatment is performed by the membrane separation treatment with the filter unit 20, but the filter unit 20 can be replaced with a treatment portion that performs the separation treatment according to a known method such as a sonic aggregation method or a centrifugation method.

As described above, according to the present disclosure, the cell culture method in which cell culture is possible at a high cell concentration, and the damage to cells is suppressed, a product producing method including the cell culture method, and a cell culture device that enables the cell culture method can be provided. In the case of the product producing method, the produced product can be used for, for example, biomedical drugs and regenerative medicine.

EXAMPLES

Hereinafter, the present disclosure will be described in detail with reference to Examples, but the present disclosure is not limited to these Examples. In present Examples, "%"

and "part" respectively mean "% by mass" and "part by mass", unless otherwise specified.

Reference Example 1: Reference Examples 1-1 to 1-4

In order to investigate the average hole diameter of the gas supply portion in the sparger, at which the damage to cells is suppressed, a fed-batch culture having a 1.2 L scale was carried out while changing the average hole diameter.

Cell damage was evaluated from the cell number and cell survival rate (viability) after culture.

<Experimental Procedure>

1.2 L of a medium (Thermo Fisher Scientific, Inc., OptiCHO™ Medium) to which glutamine (Gln) was added so that the concentration was 8 mM (mol/L) was added in a culture vessel having a total volume of 3 L.

CHO cells were seeded at a concentration of $2 \times 10^5$ cells/mL in the added medium.

The culture was carried out for 3 days (72 hours) under the conditions of a stirring rotation speed of 180 revolutions per minute (rpm), an upper surface gas Air of 15 mL/min, and $CO_2$ of 0.75 mL/min.

After the above culture for 3 days, oxygen was discharged from each sparger so that the oxygen concentration in the cell suspension was controlled to 50% (the oxygen saturation concentration in Air was set to 100%). At that time, in addition to oxygen, nitrogen was similarly flowed from the sparger so that the total gas flow rate from the sparger was 0.03 vvm.

Thereafter, the culture was controlled all the time under the above conditions until the end of the culture. The sparger used had a circular plane shape, a diameter of 6 mm, and an area of $0.000028 \ m^2$.

Further, after the above culture for 3 days, Cell Boost™ 7a (FeedA) manufactured by General Electric Company, having a liquid volume corresponding to 2% of the cell suspension volume, and Cell Boost™ 7b (FeedB) manufactured by General Electric Company, having a liquid volume corresponding to 0.2% of the cell suspension volume, were daily added once a day.

Further, the above culture was performed while measuring glucose (Glc) and Gln (glutamine) in the cell suspension. From the day 3 of the culture, 450 g/L of a Glc solution was daily added once a day at 0.75% of the cell suspension volume in a case where Glc was less than 4.0 g/L, and 200 mM of Gln was daily added once a day at 0.5% of the cell suspension volume in a case where Gln was less than 1.5 mM.

The culture was performed for a total of 14 days, and the cell number and the cell survival rate were daily evaluated by the trypan blue method using a live and dead cell autoanalyzer Vi-CELLXR (product name, manufactured by Beckman Coulter, Inc.).

Cell damage was evaluated by evaluating the highest cell density achieved for 14 days after starting oxygen supply from each sparger and the cell survival rate at day 14. The evaluation criteria are as follows, and the details of the culture conditions and the evaluation results are shown in Table 1 below.

[Evaluation Criteria]

A: The cell concentration is $2 \times 10^7$ cells/mL or more and the cell survival rate is 80% or more.

B: The cell concentration is $1 \times 10^7$ cells/mL or more, and the cell survival rate is 50% or more, but A is not applicable.

C: None A and B is applicable.

TABLE 1

| Reference Example | Sparger hole diameter [μm] | Highest cell density achieved of viable cell (×10⁷) cells/ml] | Cell survival rate at day 14 [%] | Volume average bubble diameter Dv [μm] | Sparger area/culture volume A/X [1/m] | Gas flow rate/Culture volume Q/X [vvm] | Evaluation |
|---|---|---|---|---|---|---|---|
| Reference Example 1-1 | 1000 | 3.2 | 89 | 1970 | 0.024 | 0.03 | A |
| Reference Example 1-2 | 20 | 2.5 | 81 | 242 | 0.024 | 0.03 | A |
| Reference Example 1-3 | 2 | 1 | 51 | 98 | 0.024 | 0.03 | B |
| Reference Example 1-4 | 0.5 | 0.2 | 1 | 40 | 0.024 | 0.03 | C |

Reference Example 2: Reference Examples 2-1 to 2-6

In order to investigate the oxygen flow rate vvm per culture volume, at which damage to cells was suppressed, a culture having a 1.2 L scale was carried out using different gas aeration flow rates. Cell damage was evaluated from the cell number and cell viability after culture.

<Experimental Procedure>

1.2 L of a medium (Thermo Fisher Scientific, Inc., OptiCHO™ Medium) to which Gln was added so that the concentration of Gln was 8 mM was added in a culture vessel having a total volume of 3 L.

CHO cells were seeded at a concentration of $2 \times 10^5$ cells/mL in the medium.

The culture was carried out for 3 days (72 hours) under the conditions of a stirring rotation speed of 180 rpm, an upper surface gas Air of 15 mL/min, and $CO_2$ of 0.75 mL/min.

From day 3 (after 72 hours), oxygen was discharged from a sparger including a gas supply portion having an average hole diameter of 20 μm so that the oxygen concentration in the cell suspension was controlled to 50% (the oxygen saturation concentration in Air was set to 100%). At that time, in addition to oxygen, nitrogen was similarly flowed from the sparger so that the total gas flow rate from the sparger was the value shown in Table. Thereafter, the culture was controlled all the time under the above conditions until the end of the culture. The sparger used had a circular plane shape, a diameter of 6 mm, and an area of 0.000028 m².

Further, from day 3, Cell Boost™ 7a (FeedA) manufactured by General Electric Company, having a liquid volume corresponding to 2% of the cell suspension volume, and Cell Boost™ 7b (FeedB) manufactured by General Electric Company, having a liquid volume corresponding to 0.2% of the cell suspension volume, were daily added once a day.

Further, the above culture was performed while measuring Glc and Gln in the cell suspension. From day 3 of the culture, 450 g/L of a Glc solution was daily added once a day at 0.75% of the cell suspension volume in a case where Glc was less than 4.0 g/L, and 200 mM of Gln was daily added once a day at 0.5% of the cell suspension volume in a case where Gln was less than 1.5 mM.

The culture was performed for a total of 14 days, and the cell number and the cell survival rate were daily evaluated by the trypan blue method using a live and dead cell autoanalyzer Vi-CELLXR (product name, manufactured by Beckman Coulter, Inc.).

Cell damage was evaluated by evaluating the highest cell density achieved for 14 days after starting oxygen supply from each sparger and the cell survival rate at day 14. The evaluation criteria are as follows, and the details of the culture conditions and the evaluation results are shown in Table 2 below.

[Evaluation Criteria]

A: The cell concentration is $2 \times 10^7$ cells/mL or more and the cell survival rate is 80% or more.

B: The cell concentration is $2 \times 10^7$ cells/mL or more, and the cell survival rate is 60% or more, but A is not applicable.

C: The cell concentration is $1 \times 10^7$ cells/mL or more, and the cell survival rate is 50% or more, but A is not applicable.

D: None of A, B, and C is applicable.

TABLE 2

| Reference Example | Sparger flow rate [vvm] | Highest cell density achieved of viable cells (×10⁷) [cells/ml] | Cell survival rate at day 14 [%] | Volume average bubble diameter Dv [μm] | Sparger area/culture volume A/X [1/m] | Gas flow rate/Culture volume Q/X [vvm] | Evaluation |
|---|---|---|---|---|---|---|---|
| Reference Example 2-1 | 0.01 | 3.2 | 88 | 212 | 0.024 | 0.01 | A |
| Reference Example 2-2 | 0.02 | 3.2 | 86 | 199 | 0.024 | 0.02 | A |
| Reference Example 2-3 | 0.03 | 2.5 | 81 | 248 | 0.024 | 0.03 | A |
| Reference Example 2-4 | 0.05 | 2.2 | 68 | 570 | 0.024 | 0.05 | B |
| Reference Example 2-5 | 0.1 | 1.4 | 53 | 783 | 0.024 | 0.1 | C |
| Reference Example 2-6 | 0.15 | 0.9 | 45 | 1312 | 0.024 | 0.15 | D |

About Reference Example 1 and Reference
Example 2

Reference Example 1 and Reference Example 2 are
examples in which the cell suspension volume in culture is
set to 1.2 L (=0.0012 m³).

Here, for example, in Reference Example 1 or Reference
Example 2, in a case where the cell suspension volume is
scaled up to 0.5 m³ (417 times), it is usual to set the sparger
area A to $\{(417)^{1/3}\}^2$=55.8 times from the above-described
scaling law.

In that case, the value of A/X is changed to (55.8/417)
times and thus becomes 0.0032 from the current 0.024.

For example, as shown in Comparative Example 3-7
described later, it is shown that the oxygen supply capacity
is low In a case where A/X is less than 0.004.

That is, it can be seen that for example, even in a case
where the example described in Reference Example 1 or
Reference Example 2 is simply scaled up on the basis of the
conventional technical idea, the resultant scaled-up system
has a low oxygen supply capacity, and the cell culture
method according to the present disclosure can be realized.

Examples 3-1 to 3-15 and Comparative Examples
3-1 to 3-8

A culture vessel in which the size and shape of the culture
vessel, the average hole diameter surface area, installation
position, and the like of the sparger were changed as shown
in Table 3 below was used, and the measurement or calculation of each parameter shown in Table 3 or Table 4 was
performed.

As the culture vessel, in Example 3-1 to Example 3-5,
Example 3-7 to Example 3-15, and Comparative Example
3-1 to Comparative Example 3-6, Reactor 1 was used as a
single-use culture vessel, and in Examples 3-6 and Com-
parative Examples 3-7 to 3-8, a device based on Reactor 2
was used as a single-use culture vessel.
Reactor 1

Culture tank bag diameter: 1.22 m, culture tank bag total
height: 2.3 m, liquid volume with which the culture tank is
maximally filled: 2,000 L, culture tank bag liquid level
(2,000 L): 1.83 m, stirring blade: 4 blades (blade angle, 40°),
stirring diameter: 419 mm, sparger type: sintered metal,
sparger shape: planar disc shape, sparger hole diameter: 20 μm, sparger size: 8 discs of φ25 mm, sparger installation
position: directly under the stirring blade
Reactor 2

Culture tank bag diameter: 0.96 m, culture tank bag total
height: 1.8 m, liquid volume with which the culture tank is
maximally filled: 1,000 L, culture tank bag liquid level
(1,000 L): 1.45 m, stirring blade: 3 blades (blade angle, 40°),
stirring diameter: 318 mm, sparger type: sintered metal,
sparger shape: planar disc shape, sparger hole diameter: 20
μm, sparger size: 8 discs of φ25 mm, sparger installation
position: directly under the stirring blade The bubble diameter distribution and kLa were measured
by the method described above.

In addition, in each of Examples and Comparative
Examples, In a case where the sparger is composed of a
plurality of units, the gas flow rate was adjustable for each
unit.

Further, in Table 3, the description in the column of
"Stirring rotation" indicates the rotation speed of the stirring
blade, and the description in the column of "Stirring P/V"
indicates the stirring torque (the power required for stirring
per unit liquid volume (W/m³)).

In Table 3, the description in the column of "Hole
diameter" indicates the average hole diameter of the gas
discharge portion in the sparger described above.

In Table 3, the description of "Sintered metal" in the
"Type" column indicates that the sparger has a sintered
metal filter (a sintered metal element manufactured by SMC
Corporation, made of stainless steel) in the gas discharge
portion, the description of "polyester mesh" indicates that
the sparger has a polyester mesh (PETEX, 07-350/34, manu-
factured by Sefar Filtration Inc.) in the gas discharge por-
tion, the description of "Gas permeable film" indicates that
the sparger has a gas permeable film (Tyvek© 1059B) in the
gas discharge portion.

In Table 3, the description of "Shape" indicates the shape
of the gas supply portion in the sparger; the description of
"Cylinder" indicates that the gas supply portion in the
sparger has a cylinder shape, the description of "Circular
plane" indicates that the shape of the gas discharge portion
in the sparger is a circular plane shape, and the description
of the "Quadrate plane indicates that the shape of the gas
discharge portion of the sparger is a quadrate plane shape.

In Table 3, the description in the column of "Surface area
of one sparger" indicates the average surface area per
sparger.

In Table 3, the description in the column of "Number of
units" indicates the number of sparger units used.

In Table 3, the description in the column "Number of
spargers per unit" indicates the number of spargers included
in each sparger unit.

In Table 3, the description in the column of "Total number
of spargers" indicates the number of all spargers included in
the culture vessel.

In Table 3, the description in the column "Air flow rate per
unit" indicates the flow rate of the air gas supplied to each
sparger unit.

In Table 3, in the descriptions in the columns described as
X, ZL, D, A, Zs, and Q, X, ZL, D, A, Zs, and Q are as
described above.
<Cell Damage Evaluation>

The damage to cells was estimated according to the
following evaluation criteria, and the evaluation results are
shown in Table below. From the results of Reference
Example 1 and Reference Example 2 described above, it is
speculated that the cell damage can be estimated by the
following evaluation criteria. The evaluation result prefer-
ably satisfies the evaluation criteria A, B, or C.
[Evaluation Criteria]

A: The sparger diameter is 10 μm or more, and the oxygen
flow rate is 0.03 vvm or less.

B: The sparger diameter is 2 μm or more, and the oxygen
flow rate is 0.05 vvm or less, but A is not applicable.

C: The sparger diameter is 1 μm or more, and the oxygen
flow rate is 0.1 vvm or less, but none of A and B is
applicable.

D: None of A, B, and C is applicable.
<Oxygen Supply Capacity Evaluation>

The oxygen supply capacity was estimated according to
the following evaluation criteria, and the evaluation results
are shown in Table below. It is speculated that the higher kLa
enables the culture at the higher cell concentration. The
evaluation result preferably satisfies the evaluation criteria
A, B, or C.
[Evaluation Criteria]

A: kLa is 25 or more (corresponding to a cell number of
about $8\times10^7$ cells/mL or more).

B: kLa is 20 or more and less than 25 (corresponding to a cell number of about $6×10^7$ cells/mL to $8×10^7$ cells/mL).

C: kLa is 15 or more and less than 20 (corresponding to a cell number of about $4×10^7$ cells/mL to $6×10^7$ cells/mL).

D: kLa is less than 15.

<Culture Bag Resistance>

The resistance of the culture bag was evaluated by a method described in (1) to (5) below.

As the culture bag, a culture tank bag having the diameter and the total height described in the Reactor 1 or the Reactor 2 was used. A doubled polyethylene film was used for the bag. Specifically, the bag was made so that the liquid contact surface was formed of ASIPL-01026 (thickness: about 150 μm) and the outer surface was formed of ASIPL-01029 (thickness: about 150 μm).

In a case where the sparger area is too large, the weight of the sparger increases or the joint surface between the sparger and the bag increases, and thus the load is applied to the culture bag, which causes the culture bag to be easily damaged.

(1) The culture bag is mounted in the main body of the culture tank.

(2) The above measurement solution with which the bag is maximally filled is sent to the culture bag.

(3) The solution is drained from the culture bag.

(4) The culture bag is unmounted from the culture tank.

(5) (1) to (4) are repeated until the culture bag is damaged (until holes are formed and/or the solution leaks).

The evaluation was performed according to the following evaluation criteria. The evaluation result preferably satisfies the evaluation criteria A, B, or C.

[Evaluation Criteria]

A: No damage is observed even in a case where the culture bag is mounted in and unmounted from the culture tank three times.

B: No damage is observed even in a case where the culture bag is mounted in and unmounted from the culture tank two times, but the damage is observed in a case where the culture bag is mounted in and unmounted from the culture tank three times.

C: No damage is observed even in a case where the culture bag is mounted in and unmounted from the culture tank once, but the damage is observed in a case where the culture bag is mounted in and unmounted from the culture tank two times.

D: Damage of the culture bag is observed after the first mount and unmount.

TABLE 3-1

| | Culture vessel | | | Stirring | | Sparger | | |
|---|---|---|---|---|---|---|---|---|
| | Culture | Culture | Culture | Stirring | Stirring | Surface | | |
| | volume X $m^3$ | solution height ZL m | vessel diameter D m | rotation rpm | P/V $W/m^3$ | area A $m^2$ | Hole diameter μm | Height Zs m |
| Example 3-1 | 2 | 1.83 | 1.18 | 115 | 33 | 0.046 | 20 | 0.15 |
| Example 3-2 | 2 | 1.83 | 1.18 | 115 | 33 | 0.018 | 20 | 0.15 |
| Example 3-3 | 2 | 1.83 | 1.18 | 115 | 33 | 0.009 | 20 | 0.15 |
| Example 3-4 | 2 | 1.83 | 1.18 | 115 | 33 | 0.055 | 20 | 0.15 |
| Example 3-5 | 2 | 1.83 | 1.18 | 115 | 33 | 0.183 | 20 | 0.15 |
| Example 3-6 | 1 | 1.45 | 0.94 | 124 | 33 | 0.018 | 20 | 0.15 |
| Example 3-7 | 2 | 1.83 | 1.18 | 115 | 33 | 0.046 | 2 | 0.15 |
| Example 3-8 | 2 | 1.83 | 1.18 | 115 | 33 | 0.046 | 120 | 0.15 |
| Example 3-9 | 2 | 1.83 | 1.18 | 115 | 33 | 0.046 | 20 | 0.5 |
| Example 3-10 | 2 | 1.83 | 1.18 | 115 | 33 | 0.046 | 20 | 1 |
| Example 3-11 | 2 | 1.83 | 1.18 | 115 | 33 | 0.046 | 20 | 0.15 |
| Example 3-12 | 2 | 1.83 | 1.18 | 115 | 33 | 0.046 | 20 | 0.15 |
| Example 3-13 | 2 | 1.83 | 1.18 | 115 | 33 | 0.046 | 20 | 0.15 |
| Example 3-14 | 2 | 1.83 | 1.18 | 115 | 33 | 0.040 | 20 | 0 |
| Example 3-15 | 2 | 1.83 | 1.18 | 115 | 33 | 0.039 | 20 | 0 |

TABLE 3-1-continued

| | | | Sparger | | | | | |
|---|---|---|---|---|---|---|---|---|
| | Type | Shape | Surface area of one sparger m$^2$ | Number of units unit | Number of spargers per unit unit | Total number of spargers unit | Air flow rate per unit m$^3$/min | Total flow rate Q m$^3$/min |
| Example 3-1 | Sintered metal | Cylinder | 0.0012 | 4 | 10 | 40 | 0.01 | 0.04 |
| Example 3-2 | Sintered metal | Cylinder | 0.0012 | 2 | 8 | 16 | 0.02 | 0.04 |
| Example 3-3 | Sintered metal | Cylinder | 0.0012 | 1 | 8 | 8 | 0.04 | 0.04 |
| Example 3-4 | Sintered metal | Cylinder | 0.0012 | 6 | 8 | 48 | 0.0067 | 0.04 |
| Example 3-5 | Sintered metal | Cylinder | 0.0018 | 10 | 10 | 100 | 0.004 | 0.04 |
| Example 3-6 | Sintered metal | Cylinder | 0.0012 | 2 | 8 | 16 | 0.01 | 0.02 |
| Example 3-7 | Sintered metal | Cylinder | 0.0012 | 4 | 10 | 40 | 0.01 | 0.04 |
| Example 3-8 | Sintered metal | Cylinder | 0.0012 | 4 | 10 | 40 | 0.01 | 0.04 |
| Example 3-9 | Sintered metal | Cylinder | 0.0012 | 4 | 10 | 40 | 0.01 | 0.04 |
| Example 3-10 | Sintered metal | Cylinder | 0.0012 | 4 | 10 | 40 | 0.01 | 0.04 |
| Example 3-11 | Sintered metal | Cylinder | 0.0012 | 4 | 10 | 40 | 0.0045 | 0.018 |
| Example 3-12 | Sintered metal | Cylinder | 0.0012 | 4 | 10 | 40 | 0.025 | 0.1 |
| Example 3-13 | Sintered metal | Cylinder | 0.0012 | 4 | 10 | 40 | 0.05 | 0.2 |
| Example 3-14 | Sintered metal | Circular plane | 0.0013 | 4 | 8 | 32 | 0.01 | 0.04 |
| Example 3-15 | Sintered metal | Quadrate plane | 0.0012 | 4 | 8 | 32 | 0.01 | 0.04 |

TABLE 3-2

| | Culture vessel | | | Stirring | | Sparger | | |
|---|---|---|---|---|---|---|---|---|
| | Culture volume X m$^3$ | Culture solution height ZL m | Culture vessel diameter D m | Stirring rotation rpm | Stirring P/V W/m$^3$ | Surface area A m$^2$ | Hole diameter μm | Height Zs m |
| Comparative Example 3-1 | 2 | 1.83 | 1.18 | 115 | 33 | 0.004 | 20 | 0 |
| Comparative Example 3-2 | 2 | 1.83 | 1.18 | 115 | 33 | 0.004 | 20 | 0 |
| Comparative Example 3-3 | 2 | 1.83 | 1.18 | 115 | 33 | 0.004 | 20 | 0 |
| Comparative Example 3-4 | 2 | 1.83 | 1.18 | 115 | 33 | 0.004 | 20 | 0 |
| Comparative Example 3-5 | 2 | 1.83 | 1.18 | 115 | 33 | 0.046 | 350 | 0.15 |
| Comparative Example 3-6 | 2 | 1.83 | 1.18 | 115 | 33 | 0.046 | 0.22 | 0.15 |
| Comparative Example 3-7 | 1 | 1.45 | 0.94 | 124 | 33 | 0.004 | 20 | 0 |
| Comparative Example 3-8 | 1 | 1.45 | 0.94 | 124 | 33 | 0.132 | 0.22 | 0.15 |

TABLE 3-2-continued

| | | | Sparger | | | | | |
|---|---|---|---|---|---|---|---|---|
| | Type | Shape | Surface area of one sparger m² | Number of units unit | Number of spargers per unit unit | Total number of spargers unit | Air flow rate per unit m³/min | Total flow rate Q m³/min |
| Comparative Example 3-1 | Sintered metal | Circular plane | 0.0005 | 1 | 8 | 8 | 0.04 | 0.04 |
| Comparative Example 3-2 | Sintered metal | Circular plane | 0.0005 | 1 | 8 | 8 | 0.02 | 0.02 |
| Comparative Example 3-3 | Sintered metal | Circular plane | 0.0005 | 1 | 8 | 8 | 0.1 | 0.1 |
| Comparative Example 3-4 | Sintered metal | Circular plane | 0.0005 | 1 | 8 | 8 | 0.21 | 0.21 |
| Comparative Example 3-5 | Polyester mesh | Circular plane | 0.0012 | 4 | 10 | 40 | 0.01 | 0.04 |
| Comparative Example 3-6 | Gas permeable film | Circular plane | 0.0012 | 4 | 10 | 40 | 0.01 | 0.04 |
| Comparative Example 3-7 | Sintered metal | Circular plane | 0.0005 | 1 | 8 | 8 | 0.02 | 0.02 |
| Comparative Example 3-8 | Gas permeable film | Circular plane | 0.0264 | 5 | 1 | 5 | 0.004 | 0.02 |

TABLE 4-1

| | Calculation Expression | | | | | | | Bubble diameter Volume average diameter |
|---|---|---|---|---|---|---|---|---|
| | A/X 1/m | Q/A m/min | Q/X vvm | Zs/ZL — | ZL/D — | Expression 3-1 — | Expression 5-1 s | Dv μm |
| Example 3-1 | 0.0231 | 0.87 | 0.02 | 0.082 | 1.55 | 0.79 | 67.3 | 202 |
| Example 3-2 | 0.0092 | 2.17 | 0.02 | 0.082 | 1.55 | 1.97 | 23.2 | 344 |
| Example 3-3 | 0.0046 | 4.34 | 0.02 | 0.082 | 1.55 | 3.94 | 10.2 | 520 |
| Example 3-4 | 0.0277 | 0.73 | 0.02 | 0.082 | 1.55 | 0.66 | 48.9 | 237 |
| Example 3-5 | 0.0914 | 0.22 | 0.02 | 0.082 | 1.55 | 0.20 | 11.4 | 490 |
| Example 3-6 | 0.0185 | 1.08 | 0.02 | 0.104 | 1.54 | 0.99 | 69.4 | 175 |
| Example 3-7 | 0.0231 | 0.87 | 0.02 | 0.082 | 1.55 | 0.79 | 339.2 | 90 |
| Example 3-8 | 0.0231 | 0.87 | 0.02 | 0.082 | 1.55 | 0.79 | 16.3 | 410 |
| Example 3-9 | 0.0231 | 0.87 | 0.02 | 0.273 | 1.55 | 0.79 | 50.8 | 207 |
| Example 3-10 | 0.0231 | 0.87 | 0.02 | 0.547 | 1.55 | 0.79 | 30.5 | 211 |
| Example 3-11 | 0.0231 | 0.39 | 0.009 | 0.082 | 1.55 | 0.35 | 47.7 | 240 |
| Example 3-12 | 0.0231 | 2.17 | 0.05 | 0.082 | 1.55 | 1.97 | 24.3 | 336 |
| Example 3-13 | 0.0231 | 4.34 | 0.1 | 0.082 | 1.55 | 3.94 | 5.3 | 722 |
| Example 3-14 | 0.0201 | 1.00 | 0.02 | 0.000 | 1.55 | 0.90 | 52.0 | 240 |
| Example 3-15 | 0.0196 | 1.02 | 0.02 | 0.000 | 1.55 | 0.93 | 42.3 | 266 |

TABLE 4-1-continued

| | Bubble diameter Cumulative volume ratio of air bubbles having bubble diameter of 20 μm to 500 μm % | kLa kLa hr$^{-1}$ | kLa Surmised cell concentration (×10$^7$ cells/ml) | Evaluation Cell damage | Evaluation Oxygen supply capacity | Evaluation Culture bag resistance |
|---|---|---|---|---|---|---|
| Example 3-1 | 92 | 28 | 8.6 | A | A | A |
| Example 3-2 | 81 | 22 | 6.8 | A | B | A |
| Example 3-3 | 45 | 16 | 4.9 | A | C | A |
| Example 3-4 | 89 | 28 | 8.6 | A | A | B |
| Example 3-5 | 63 | 24 | 7.4 | A | B | C |
| Example 3-6 | 92 | 24 | 7.4 | A | B | A |
| Example 3-7 | 92 | 29 | 8.9 | B | A | A |
| Example 3-8 | 71 | 22 | 6.8 | A | B | A |
| Example 3-9 | 92 | 23 | 7.1 | A | B | A |
| Example 3-10 | 92 | 16 | 4.9 | A | C | A |
| Example 3-11 | 88 | 16 | 4.9 | A | C | A |
| Example 3-12 | 77 | 38 | 11.7 | B | A | A |
| Example 3-13 | 34 | 48 | 14.8 | C | A | A |
| Example 3-14 | 90 | 29 | 8.9 | A | A | A |
| Example 3-15 | 90 | 29 | 8.9 | A | A | A |

TABLE 4-2

| | Calculation Expression A/X 1/m | Calculation Expression Q/A m/min | Calculation Expression Q/X vvm | Calculation Expression Zs/ZL — | Calculation Expression ZL/D — | Calculation Expression Expression 3-1 — | Calculation Expression Expression 5-1 s | Bubble diameter Volume average diameter Dv μm |
|---|---|---|---|---|---|---|---|---|
| Comparative Example 3-1 | 0.0020 | 10.19 | 0.02 | 0.000 | 1.55 | 9.27 | 0.8 | 1950 |
| Comparative Example 3-2 | 0.0020 | 5.10 | 0.01 | 0.000 | 1.55 | 4.63 | 3.9 | 880 |
| Comparative Example 3-3 | 0.0020 | 25.48 | 0.05 | 0.000 | 1.55 | 23.17 | 0.4 | 2700 |
| Comparative Example 3-4 | 0.0020 | 53.50 | 0.105 | 0.000 | 1.55 | 48.65 | 0.3 | 3300 |
| Comparative Example 3-5 | 0.0231 | 0.87 | 0.02 | 0.082 | 1.55 | 0.79 | 3.5 | 890 |
| Comparative Example 3-6 | 0.0231 | 0.87 | 0.02 | 0.082 | 1.55 | 0.79 | 1717.4 | 40 |
| Comparative Example 3-7 | 0.0039 | 5.10 | 0.02 | 0.000 | 1.54 | 4.63 | 3.0 | 890 |
| Comparative Example 3-8 | 0.1320 | 0.15 | 0.02 | 0.104 | 1.54 | 0.14 | 1263.9 | 41 |

TABLE 4-2-continued

| | Bubble diameter Cumulative volume ratio of air bubbles having bubble diameter of 20 μm to 500 μm % | kLa hr$^{-1}$ | Surmised cell concentration (×10$^7$ cells/ml) | Cell damage | Oxygen supply capacity | Culture bag resistance |
|---|---|---|---|---|---|---|
| | | | | | Evaluation | |
| Comparative Example 3-1 | 10 | 9.5 | 2.9 | A | D | A |
| Comparative Example 3-2 | 33 | 8.4 | 2.6 | A | D | A |
| Comparative Example 3-3 | 5 | 12 | 3.7 | B | D | A |
| Comparative Example 3-4 | 3 | 13 | 3.9 | D | D | A |
| Comparative Example 3-5 | 29 | 11 | 3.4 | A | D | A |
| Comparative Example 3-6 | 48 | 22 | 6.8 | D | B | A |
| Comparative Example 3-7 | 33 | 12 | 3.7 | A | D | A |
| Comparative Example 3-8 | 28 | 19 | 5.8 | D | C | C |

In Table 3, the description in the column of "Culture vessel diameter" indicates the equivalent circle diameter of the culture vessel calculated according to Expression $(4 \times X/ZL/3.14)^{0.5}$.

In Table 4, the description in the column of "ZL/D" indicates the value of $ZL/(4 \times X/ZL/3.14)^{0.5}$ in Expression 6-2.

In addition, in Table 4, the description in the column of "Expression 3-1" indicates the value of $(Q/A/60)/[\{3 \times 10^{-8} \times (\rho L - \rho g) \times g\}/(18 \times \mu L)\}]$ in Expression 3-1.

In addition, in Table 4, the description in the column of "Expression 5-1" indicates the value of $\{Dv^2 \times 10^{-12} \times (\mu L - \rho g) \times g/(18 \times \mu L)\}$ in Expression 5-1.

In Table 4, for the calculation, a gravitational acceleration g=9.8 m/s$^2$, a measurement solution density ρL (kg/m3)=1, 000 kg/m$^3$, an air gas density ρg=1.293 kg/m$^3$, and a measurement solution viscosity μL=8.9×10$^{-4}$ kg/m/s are used.

In Table 4, the description in the column of "Cumulative volume ratio of bubbles having bubble diameter 20 m to 500 m" indicates the ratio of the cumulative volume of air bubbles having a bubble diameter of 20 μm to 500 μm with respect to the total volume of the bubbles in the bubble diameter distribution.

In Table 4, the description in the column of "Surmised cell concentration" indicates the cell concentration estimated from the contents of Reference Example 1 and Reference Example 2 and the measured kLa value.

In Table 4, the descriptions in the columns described as A/X, Q/A, Q/X, Zs/ZL, Dv, and kLa respectively indicate the values of the corresponding parameters described above.

From the results shown in Table 3 and Table 4, it can be seen that the cell culture method according to the present disclosure enables cell culture at a high cell concentration even in a case where the cell suspension volume is large, and the damage to cells is suppressed.

The disclosure of JP2018-122322 filed on Jun. 27, 2018, is incorporated herein by reference in its entirety.

All documents, patent applications, and technical standards described in the present specification are incorporated herein by reference, to the same extent as in the case where each of the documents, patent applications, and technical standards is specifically and individually described.

EXPLANATION OF REFERENCES

10: sparger (sintered metal sparger)
11: stirring blade
12: sintered metal filter
14: support portion
16: gas supply portion
20: filter unit
20*a*: inlet
20*b*: outlet
20*c*: ejection outlet
21: vessel
22: supply side
23: permeation side
24: filter membrane
40: collection tank
51: to 56 flow channels
60: pressure gauge
62, 64, 66, 68, 70, 74, 76: arrows
100: culture vessel
102: cell suspension
104: inner bottom surface
110: sparger unit
112: gas supply portion
200: cell culture device
PU1 to PU3: pumps
A: fresh medium supply port
B: migration of cell suspension used for cell bleeding treatment
C: migration of permeated liquid used for purification treatment
V pinch valve
What is claimed is:
1. A cell culture method comprising:
using a culture vessel which contains a cell suspension; and
discharging a gas including 30% by volume or more of oxygen into the cell suspension from a sparger disposed in the culture vessel to culture the cells, wherein a plurality of spargers are included as the sparger, an average hole diameter of a gas discharge portion in each of the spargers is 1 m or more and 300 m or less, and a surface area A (m$^2$) of the gas discharge portion in the sparger, a volume X (m$^3$) of the cell suspension in the culture vessel, and a flow rate Q (m$^3$/min) of the gas that is discharged from the sparger satisfy Expression 1-1, Expression 1-2, and Expression 1-3, wherein $$0.004 \leq A/X \leq 0.025, \quad \text{Expression 1-1}$$

$$X \geq 0.5, \text{ and} \quad \text{Expression 1-2}$$

$$0.001 \leq Q/X \leq 0.05 \quad \text{Expression 1-3}$$

wherein a cell concentration in the cell suspension is $4 \times 10^7$ cells/mL or more.

2. The cell culture method according to claim 1, wherein a bubble diameter distribution in a gas discharge outlet of the sparger is measured by replacing the cell suspension in the culture vessel with a measurement solution which is pure water containing 1 g/L of poloxamer 188, 7 g/L of sodium chloride, and sending 2 g/L of sodium hydrogen carbonate, an air gas having the same flow rate as the Q (m$^3$/min) in the culture from the sparger to the measurement solution, where a volume-average diameter Dv (μm) of bubbles of the air gas satisfies Expression 2-1, wherein $$50 \leq Dv \leq 800 \quad \text{Expression 2-1.}$$

3. The cell culture method according to claim 1, wherein a bubble diameter distribution in a gas discharge outlet of the sparger is measured by replacing the cell suspension in the culture vessel with a measurement solution which is pure water containing 1 g/L of poloxamer 188, 7 g/L of sodium chloride, and 2 g/L of sodium hydrogen carbonate, and sending an air gas having the same flow rate as the Q (m$^3$/min) in the culture from the sparger to the measurement solution, where a proportion of a cumulative volume of air bubbles having a bubble diameter of 20 m or more and 500 m or less is 30% by volume or more of a total volume of the bubbles in the bubble diameter distribution.

4. The cell culture method according to claim 1, wherein an oxygen transfer capacity coefficient kLa (hr$^{-1}$) by the sparger in the culture is 22 or more.

5. The cell culture method according to claim 1, wherein a bubble diameter distribution in a gas discharge outlet of the sparger is measured by replacing the cell suspension in the culture vessel with a measurement solution which is pure water containing 1 g/L of poloxamer 188, 7 g/L of sodium chloride, and 2 g/L of sodium hydrogen carbonate, and sending an air gas having the same flow rate as the Q (m$^3$/min) in the culture from the sparger to the measurement solution, where the Q (m$^3$/min), the A (m$^2$), a density ρL (kg/m$^3$) of the measurement solution, a density ρg (kg/m$^3$) of the air gas, a viscosity μL (kg/m/s) of the measurement solution, and a gravitational acceleration g (m/s$^2$) satisfy Expression 3-1, wherein $$0.1 < (Q/A/60)/[\{3 \times 10^{-8} \times (\rho L - \rho g) \times g\}/(18 \times \mu L)\}] \leq 5 \quad \text{Expression 3-1.}$$

6. The cell culture method according to claim 1, wherein in the culture, the Q (m$^3$/min) and the A (m$^2$) satisfy Expression 4-1, wherein $$0.1 \leq Q/A \leq 5 \quad \text{Expression 4-1.}$$

7. The cell culture method according to claim 1, wherein a bubble diameter distribution in a gas discharge outlet of the sparger is measured by replacing the cell suspension in the culture vessel with a measurement solution which is pure water containing 1 g/L of poloxamer 188, 7 g/L of sodium chloride, and 2 g/L of sodium hydrogen carbonate, and sending an air gas having the same flow rate as the Q (m$^3$/min) in the culture from the sparger to the measurement solution, where a liquid level ZL (m) from an inner bottom surface of the culture vessel to an upper surface of the cell suspension in the culture, a height Zs (m) from the inner bottom surface of the culture vessel to a sparger installation surface, a volume average bubble diameter Dv (μm) of bubbles in the bubble diameter distribution, a density ρL (kg/m$^3$) of the measurement solution, a density ρg (kg/m$^3$) of the air gas, a gravitational acceleration g (m/s$^2$), and a viscosity μL (kg/m/s) of the measurement solution satisfy Expression 5-1, wherein $$2 < (ZL - Zs)/\{Dv^2 \times 10^{-12} \times (\rho L - \rho g) \times g/(18 \times \mu L)\} \leq 300 \quad \text{Expression 5-1.}$$

8. The cell culture method according to claim 1, wherein the X (m$^3$), a liquid level ZL (m) from an inner bottom surface of the culture vessel to an upper surface of the cell suspension, and a height Zs (m) from the inner bottom surface of the culture vessel to a sparger installation surface satisfy Expression 6-1 and Expression 6-2, wherein $$Zs/ZL \leq 0.5, \text{ and} \quad \text{Expression 6-1}$$

$$0.5 \leq ZL/(4 \times X/ZL/3.14)^{0.5} \leq 4 \quad \text{Expression 6-2.}$$

9. The cell culture method according to claim 1, wherein the cell culture is a perfusion culture.

10. The cell culture method according to claim 1, wherein the culture vessel is a single-use culture tank.

11. The cell culture method according to claim 1, wherein the sparger is a sintered metal sparger.

12. The cell culture method according to claim 1, wherein a shape of the gas discharge portion of the sparger is a circular plane shape, a polygonal plane shape, or a cylinder shape.

13. The cell culture method according to claim 1, wherein the sparger is configured to include a plurality of units each including one or more spargers, and the flow rate of the gas is adjusted for each of the units.

14. The cell culture method according to claim 1, wherein the volume X (m$^3$) of the cell suspension in the culture vessel satisfies Expression 1-2, wherein $$X \geq 1.1 \quad \text{Expression 1-2.}$$

15. The cell culture method according to claim 1, wherein a total value of the surface area of the gas discharge portion in the sparger which satisfies the average hole diameter is 60% by area or more.

16. A product producing method comprising:

culturing cells with the cell culture method according to claim 1, and obtaining a product produced by the cultured cells.

17. The product producing method according to claim 16, wherein the product is an antibody.

* * * * *